United States Patent
West et al.

(10) Patent No.: US 11,013,752 B2
(45) Date of Patent: May 25, 2021

(54) COMBINATION THERAPIES FOR INNER EAR SENSORY HAIR CELL REGENERATION/REPLACEMENT

(71) Applicant: Hough Ear Institute, Oklahoma City, OK (US)

(72) Inventors: Matthew B. West, Choctaw, OK (US); Richard D. Kopke, Oklahoma City, OK (US)

(73) Assignee: HOUGH EAR INSTITUTE, Oklahoma City, OK (US)

( * ) Notice: Subject to any disclaimer, the term of this patent is extended or adjusted under 35 U.S.C. 154(b) by 0 days.

(21) Appl. No.: 15/612,872

(22) Filed: Jun. 2, 2017

(65) Prior Publication Data

US 2017/0348346 A1 Dec. 7, 2017

Related U.S. Application Data

(60) Provisional application No. 62/345,740, filed on Jun. 3, 2016.

(51) Int. Cl.

| | |
|---|---|
| *C12N 15/11* | (2006.01) |
| *A61K 31/7105* | (2006.01) |
| *A61K 9/51* | (2006.01) |
| *A61K 31/713* | (2006.01) |
| *A61K 45/06* | (2006.01) |
| *A61K 9/00* | (2006.01) |
| *A61K 9/16* | (2006.01) |
| *A61K 31/404* | (2006.01) |
| *A61K 31/433* | (2006.01) |
| *A61K 38/18* | (2006.01) |
| *A61K 41/00* | (2020.01) |
| *C12N 15/113* | (2010.01) |

(52) U.S. Cl.
CPC ........ *A61K 31/7105* (2013.01); *A61K 9/0009* (2013.01); *A61K 9/0046* (2013.01); *A61K 9/1647* (2013.01); *A61K 9/5153* (2013.01); *A61K 31/404* (2013.01); *A61K 31/433* (2013.01); *A61K 31/713* (2013.01); *A61K 38/1825* (2013.01); *A61K 41/00* (2013.01); *A61K 45/06* (2013.01); *C12N 15/113* (2013.01); *C12N 2310/14* (2013.01); *C12N 2310/3517* (2013.01); *C12N 2320/31* (2013.01); *C12N 2320/32* (2013.01)

(58) Field of Classification Search
CPC .............. A61K 2300/00; A61K 31/713; C12N 15/113; C12N 2310/14
See application file for complete search history.

(56) References Cited

U.S. PATENT DOCUMENTS

| 9,101,647 B2 | 8/2015 | Kopke |
|---|---|---|
| 2003/0232759 A1 | 12/2003 | Gao |
| 2005/0288292 A1 | 12/2005 | Bieberschulte et al. |
| 2006/0030042 A1 | 2/2006 | Brivanlou et al. |
| 2011/0217274 A1 | 9/2011 | Reid |
| 2013/0052134 A1* | 2/2013 | Duan ................. A61K 47/6935 424/9.1 |
| 2013/0210889 A1 | 8/2013 | Kopke |
| 2014/0005195 A1 | 1/2014 | Palomo Nicolau et al. |
| 2015/0018404 A1* | 1/2015 | Feinstein ............. C12N 15/113 514/44 A |
| 2015/0126507 A1* | 5/2015 | Thies ................... A61K 31/427 514/233.5 |
| 2017/0071937 A1* | 3/2017 | Karp ...................... A61K 31/55 |
| 2019/0010449 A1* | 1/2019 | Edge ................. G01N 33/5058 |
| 2019/0017015 A1 | 1/2019 | Karp et al. |
| 2019/0100790 A1 | 4/2019 | Van de Stolpe et al. |
| 2019/0142969 A1 | 5/2019 | Chen et al. |

FOREIGN PATENT DOCUMENTS

| WO | WO-2010/060088 A2 | 5/2010 |
|---|---|---|
| WO | WO 2016/069906 A1 | 5/2016 |
| WO | WO 2018/204226 A1 | 11/2018 |
| WO | WO 2019/053727 A1 | 3/2019 |

OTHER PUBLICATIONS

D'Sa et al., Plasticity of synaptic endings in the cochlear nucleus following noise-induced hearing loss is facilitated in the adult FGF2 overexpressor mouse, European Journal of Neuroscience, vol. 26, pp. 666-680. (Year: 2007).*

Murano et al., Hes1 promotes the IL-22-mediated antimicrobial response by enhancing STAT3-dependent transcription in human intestinal epithelial cells, BBRC, vol. 443, pp. 840-846. (Year: 2014).*

Lu et al., The influence of glycogen synthase kinase 3 in limiting cell addition in the mammalian ear, Developmental Neurobiology, vol. 68, pp. 1059-1075. (Year: 2008).*

Shi et al., beta-catenin is required for hair-cell differentiation in the cochlea, The Journal of Neuroscience, vol. 34, pp. 6470-6479. (Year: 2014).*

Roccio et al., Cell cycle reactivation of cochlear progenitor cells in neonatal FUCCI mice by a GSK3 small molecule inhibitor, Scientific Reports, vol. 5:17886, pp. 1-11. (Year: 2015).*

Akiyama, et al., In situ tissue engineering with synthetic self-assembling peptide nanofiber scaffolds, PuraMatrix, for mucosal regeneration in the rat middle-ear, *Intern. Journ. of Nanomedicine*, vol. 8, pp. 2629-2640 (2013).

Ariana, et al., "Modeled Analysis of Entrance of colloid Suspensions into the Middle Ear Cavity," *Otolaryngology-Head and Neck Surgery*, vol. 154, No. 5, pp. 917-919 (May 2016).

Bartlett et al., "Insights into the kinetics of siRNA-mediated gene silencing from live-cell and live-animal bioluminescent imaging," *Nucleic Acids Research*, vol. 34, No. 1, pp. 322-333 (2006).

(Continued)

Primary Examiner — Dana H Shin
(74) Attorney, Agent, or Firm — Foley & Lardner LLP

(57) ABSTRACT

The present disclosure relates to compositions and methods for the regeneration and/or restoration of hair cells utilizing a composition or an agent that decreases expression of a gene in a tissue of the inner ear and a second agent.

26 Claims, 42 Drawing Sheets
(17 of 42 Drawing Sheet(s) Filed in Color)
Specification includes a Sequence Listing.

(56) References Cited

OTHER PUBLICATIONS

Bartlett, et al., "Effect of siRNA nuclease stability on the in vitro and in vivo kinetics of siRNA-mediated gene silencing," vol. 97, No. 4, pp. 909-921 (Jul. 2007), [Abstract].
Chan et al., "Polymeric Nanoparticles for Drug Delivery," *Cancer Nanotechnology, Methods in Molecular Biology*, vol. 624, pp. 163-175 (2010).
Chiu et al., "Visualizing a Correlation between siRNA Localization, Cellular Uptake, and RNAi in Living Cells," *Chemistry & Bilogy*, vol. 11, pp. 1165-1175 (Aug. 2004).
Cun et al., "Preparation and characterization of poly(DL-lactide-co-glycolide) nanoparticles for SiRNA delivery," *Intern. Journ. of Pharmaceutics*, vol. 390, pp. 70-75 (2010).
Du et al., "Regeneration of mammalian cochlear and vestibular hair cells through Hes1/Hes5 modulcation with siRNA," *Hearing Research*, vol. 304, pp. 91-110 (2013).
Fakhr, et al., "Precise and efficient siRNA design: a key point in competent gene silencing," *Cancer Gene Therapy*, vol. 23, No. 4, pp. 73-82 (Apr. 2016), [Abstract].
Hed, "Methods for distinguishing ingested from adhering particles," *Methods in Ezymology*, vol. 132, pp. 198-204 (1986), [Abstract].
Katoh et al., "Cross-talk of WNT and FGF Signaling Pathways at GSK3β to Regulate β-Catenin and SNAIL Signaling Cascades," *Cancer Biology & Therapy*, vol. 5, No. 9, pp. 1059-1064 (Sep. 2006).
Kechai et al., "Hyaluronic acid liposomal gel sustains delivery of a corticoid to the inner ear," *Journ. of Controlled Release*, vol. 226, pp. 248-257 (Mar. 2016), [Abstract].
Li, "A Novel Aerosol-Mediated Drug Delivery System for Inner Ear Therapy: Intratympanic Aerosol methylprednisolone can Attenuate Acoustic Trauma," *IEEE Transactions on Biomedical Engineering*, vol. 60, No. 9, pp. 2450-2460 (Sep. 2013).
Livak et al., "Analysis of Relative Gene Expression Data Using Real-Time Quantitative PCR and the $2^{-\Delta\Delta C_T}$ Method," *Methods*, vol. 25, pp. 402-408 (2001).
McCall et al., "PLGA Nanoparticles Formed by Single- or Double-emulsion with Vitamin E-TPGS," *J. Vis. Exp.*, vol. 82, e51015, 8 pages (Dec. 2013).
Morales-Garcia et al., "Glycogen Synthase Kinase 3 Inhibition Promotes Adult Hippocampal Neurogenesis in Vitro and in Vivo," *ACS chemical Neuroscience*, vol. 3, pp. 963-971 (2012).
Narayan et al., "Sequentially releasing dual-drug-loaded PLGA—casein core/shell nanomedicine: Design, synthesis, biocompatibility and pharmacokinetics," *Acta Biomaterialia*, vol. 10, No. 5, pp. 2112-2124 (May 2014) [Abstract].
Parra et al., "Optimal dose of Amoxicillin in Treatment of Otitis Media Caused by a Penicillin-Resistant Pneumococcus Strain in the Gerbil Model," *Antimicrobial Agents and Chemotherapy*, pp. 859-862 (Mar. 2002).
Wei et al., "RNA-Induced Silencing Complex-Bound Small Interfering RNA is a Determinant of RNA Interference-Mediated Gene Silencing in Mice," *Molecular Pharmacology*, vol. 79, No. 6, pp. 953-963 (2011).
Winterstein, et al., "Sensorineural hearing loss associated with neomycin eardrops and nonintact tympanic membranes," *Otolaryngol Head Neck Surg.*, vol. 148, No. 2, pp. 277-283 (Dec. 2012), [Abstract].
Yang et al., "Microfluidic-assisted synthesis of hemispherical and discoidal chitosan microparticles at an oil/water interface," vol. 33, No. 21, pp. 3173-3180 (2012), [Abstract].
International Search Report and Written Opinion issued in related International Patent Application No. PCT/US2017/035673, dated Nov. 3, 2017.
International Preliminary Report on Patentability issued in related International Patent Application No. PCT/US2017/035673, dated Dec. 13, 2018.
Mittal, et al. "Signaling in the Auditory System: Implications in Hair Cell Regeneration and Hearing Function" *Cellular Physiology*, pp. 2710-2721 (Nov. 2016). [Abstract].
Czajkowksi, et al. "Pluripotent Stem-Cell Derived Cochlear Cells: A Challenge in Constant Progress." Cellular and Molecular Life Sciences, 9 pages (Feb. 2019).
Aria et al., "Hes1 Inhibitor Isolated by Target Protein Oriented Natural Products Isolation (TPO-NAPI) of Differentiation Activators of Neural Stem Cells", Chemical Science, vol. 7, No. 2, Jan. 2016, pp. 1514-1520.
Aria et al., "The First Hes1 Dimer Inhibitors for Natural Products", Bioorganic & Medicinal Chemistry Letters, vol. 19, No. 19, Oct. 2009, pp. 5778-5781.
Foreign Search Report on EP 17807565.1 dated Mar. 2, 2020.
Wei et al., "Both Strands of siRNA Have Potential to Guide Posttranscriptional Gene Silencing in Mammalian Cells," *PLoS One*, vol. 4, No. 4, 10 pages (2009).
Kopan, "Notch: A Membrane-Bound Transcription Factor," *Journ. of Cell Science*, pp. 1095-1097 (2002).

\* cited by examiner

FIG. 1A  Inner Ear (Overview)
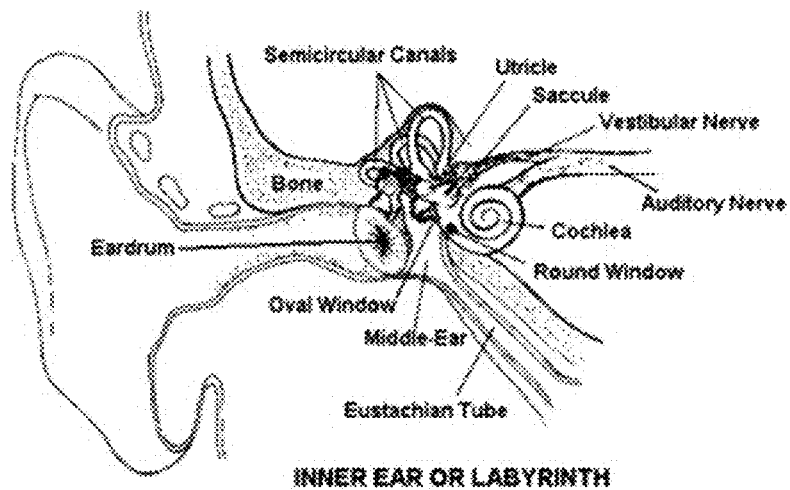
INNER EAR OR LABYRINTH
FIG. 1B  Organ of Corti (Overview)
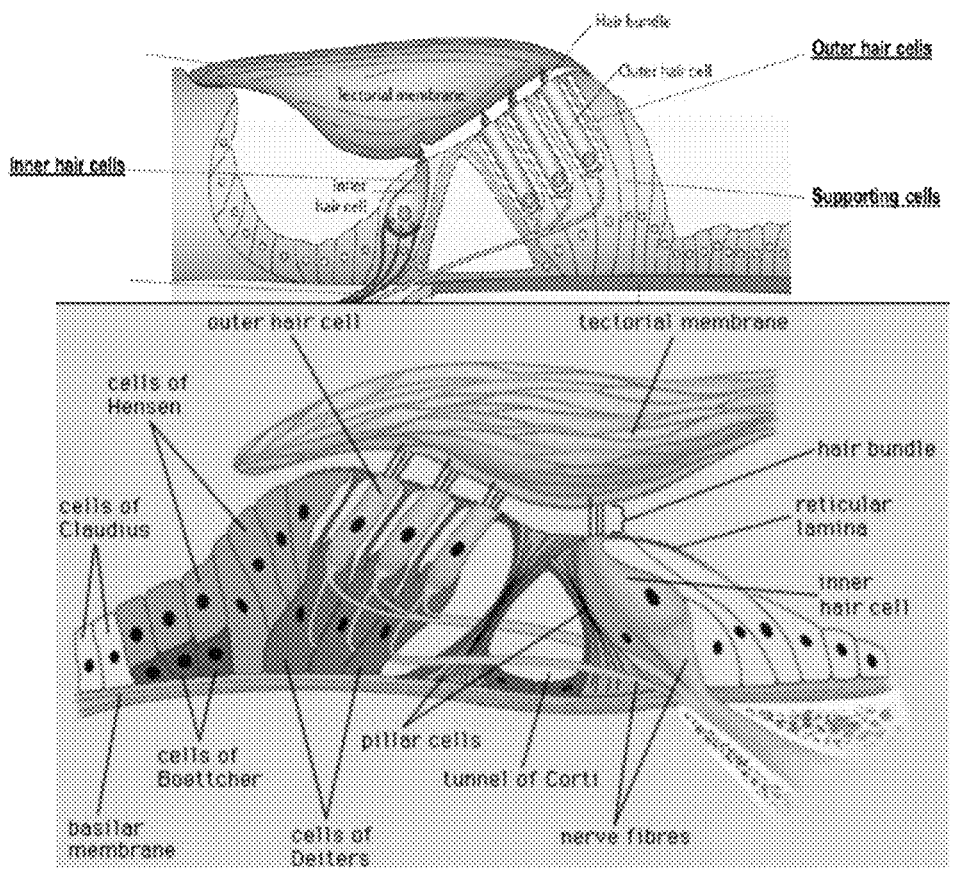

FIG. 1C Choclea (Overview and components)
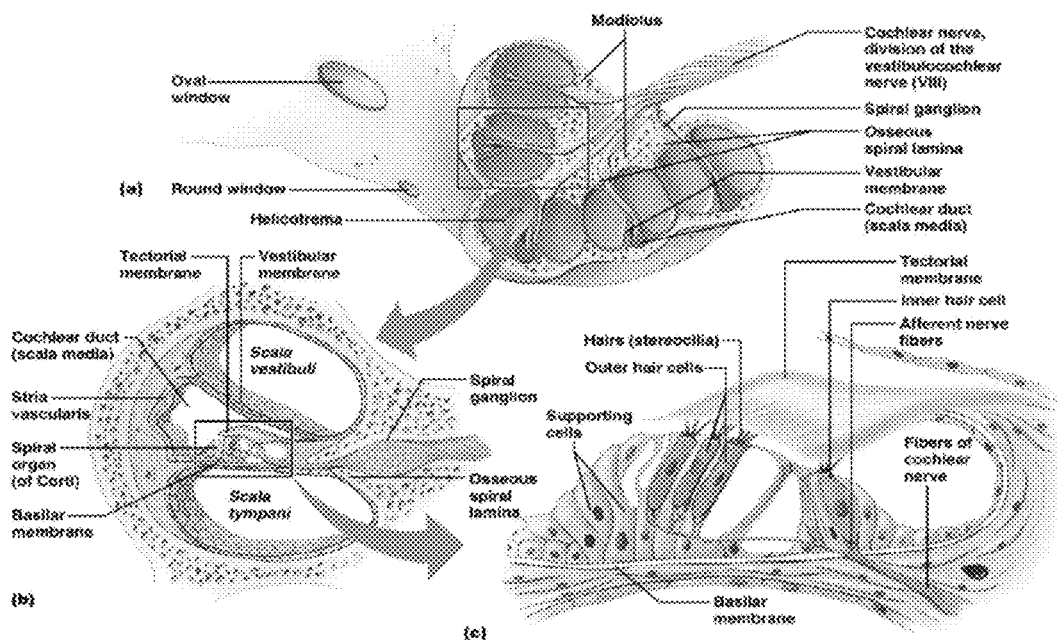
**FIG. 1D Vestibular System (Overview, *e.g.* utricles, etc.)**
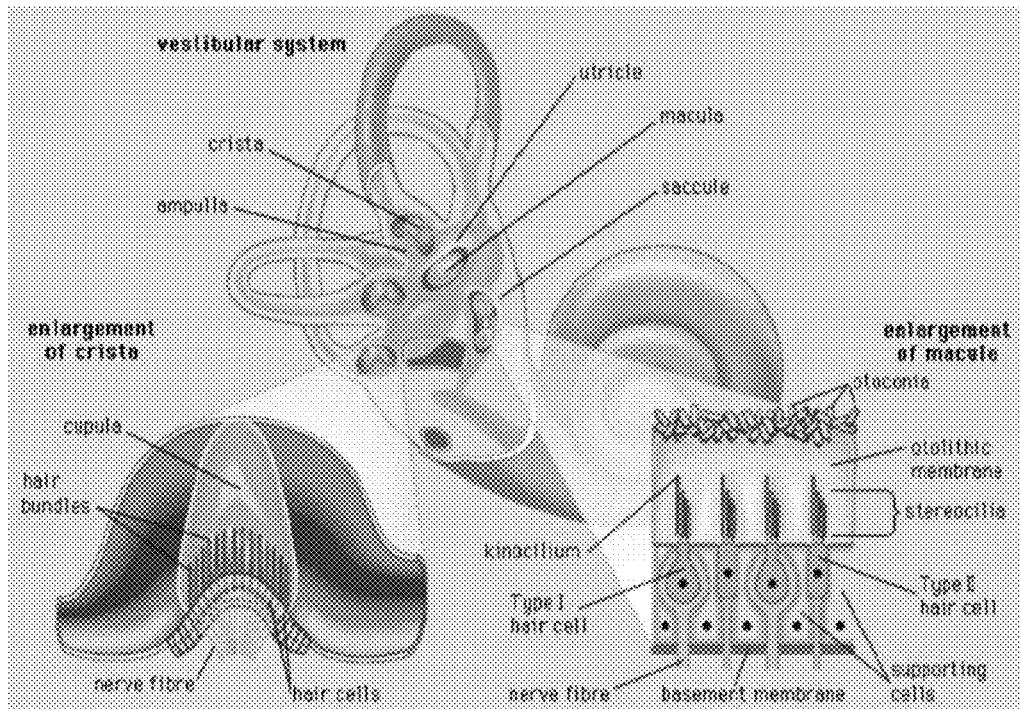

Initial burst <20% on Day 2

Middle-Apical turn as fixed reference

*Middle turn as fixed reference*

COMBINATION THERAPIES FOR INNER EAR SENSORY HAIR CELL REGENERATION/REPLACEMENT

CROSS-REFERENCE TO RELATED APPLICATIONS

This application claims priority under 35 U.S.C. 119(e) to U.S. Ser. No. 62/345,740, filed Jun. 3, 2016, the entirety of which is incorporated by reference herein.

SEQUENCE LISTING

The instant application contains a Sequence Listing which has been submitted electronically in ASCII format and is hereby incorporated by reference in its entirety.

BACKGROUND

Deafness and balance dysfunction are common human disabilities. In the majority of cases these disabilities result from the loss of sensory hair cells in the (1) organ of Corti (OC) in the cochlea, (2) the vestibular epithelium in the cristae or (3) saccule or utricle of the vestibular organ. Currently there is no FDA approved treatment that can cure these disorders by restoring the sensory hair cells in these tissues.

Current approaches to the problem involve vestibular rehabilitation to allow adaptation to the injury to the vestibular organs. The rehabilitation is time consuming and does not restore lost function. For sensorineural deafness, rehabilitation can be achieved with hearing aids or cochlear implants. However, these devices are expensive, produce a subnormal sound quality and only partial return of function, and may require an extensive surgery in the case of cochlear implants.

Another approach in treating hearing disorders is administration of peptides or other small molecules. Often treatment results are limited with the use of such agents due to the relatively high cochlear concentrations that must be achieved (micro- or millimolar). Moreover, protein or peptide inhibitors are difficult to deliver systemically to treat the ear due to the blood labyrinthine barrier and protein clearance in the bloodstream, as well as potential antigenicity. Difficulties also exist in terms of delivering adequate concentrations of peptide and protein directly to the cochlea, as well, particularly using topical delivery due to the size of the molecule.

One potential alternative to these traditional approaches is using targeted gene therapy to induce inner ear hair cell regeneration and replacement. For example, hair cell regeneration or replacement has been achieved in rodents through the use of a viral vector to introduce the Atoh1 gene into inner ear sensory epithelium. However, this approach carries risk inherent in viral vector therapy, including the induction of infection, an inflammatory immune response, genetic mutation, development of neoplasia and others. Silencing of kip1p27 RNA has been shown to induce hair cell regeneration but in an ectopic fashion without return of function. Modulation of the retinoblastoma gene can also produce additional hair cells, but there may be danger inherent in manipulating an oncogene, or cancer causing gene. Thus, current gene therapies directed to regeneration or replacement of inner ear hair cells have failed to identify a safe and effective molecular target and delivery method.

One potential gene therapy approach is through the use of short interfering RNA (siRNA). Once introduced into a cell, the siRNA molecules complex with the complimentary sequences on the messenger RNA (mRNA) expressed by a target gene. The formation of this siRNA/mRNA complex results in degradation of the mRNA through a natural intracellular process known as RNA interference (RNAi). RNAi is a well-established tool for identifying the function of a gene in a particular cellular process and for identifying potential therapeutic targets in disease models. Although RNAi has traditionally been used in cell culture and in vitro applications, gene therapy-based therapeutics are now being explored that utilize this process.

As discussed above, several gene targets have been explored with respect to regeneration of hair cells of the inner ear without much success. The basic helix-loop-helix (bHLH) genes Hes1 and Hes5 have been identified as playing roles in sensory hair cell development in the cochlea and vestibular structures of the ear. In addition, a potential gene target for preventing loss of hair cells is mitogen-activated protein kinase 1 (MAPK1), which plays a role in programmed cell death or apoptosis.

Glycogen synthase kinase 3 (GSK-3) is a serine/threonine protein kinase that mediates the addition of phosphate molecules onto serine and threonine amino acid residues. It is a kinase for over forty different proteins in a variety of different pathways and has been implicated in a variety of diseases. Thus, GSK-3 inhibitors (GSK3Is) have been tested for safety and efficacy in animal models; however, the role that inhibition of GSK-3 might play across various signaling cascades remains poorly understood.

SUMMARY

The present disclosure relates to compositions and methods for the regeneration and/or restoration of hair cells utilizing a composition or an agent that decreases expression of a gene in a tissue of the inner ear and a second agent.

In some embodiments, the gene is Hes1, Hes5, or MAPK1.

In some embodiments, the composition or agent that decreases expression of a gene in a tissue of the inner ear may include a siRNA molecule. In some embodiments, the composition or agent that decreases expression of a gene in a tissue of the inner ear may include an inhibitor of the pathway by which the gene is regulated, e.g. a Notch signaling pathway inhibitor such as gamma secretase inhibitor (since transcription of for example, Hes1, is mediated by Notch signaling).

In some embodiments, the second agent is a priming composition. In some embodiments, the priming composition exhibits one or more functions selected from the group consisting of stabilizing β catenin, increasing the number of pluripotent cells in the inner ear, increasing plasticity of pre-existing pluripotent cells in the inner ear, or signaling differentiation in cells of the inner ear. In some embodiments, this second agent is a GSK-3 inhibitor. In further embodiments, the GSK-3 inhibitor is any one or more of CHIR99021, 6-bromoindirubin-3'-oxime (BIO), or tideglusib (TIDE).

In some embodiments, the composition that decreases expression of a gene in a tissue of the inner ear may include a nanoparticle, which in turn may include an agent that decreases expression of a gene in a tissue of the inner ear.

In some embodiments, the nanoparticle encapsulates an agent that decreases expression of a gene in a tissue of the inner ear.

In some embodiments, the nanoparticle comprises a biodegradable polymer. In further embodiments, the biodegradable polymer is poly(lactic-co-glycolic acid) (PLGA) or pegylated PLGA (PEG-PLGA).

In some embodiments, the nanoparticle is magnetically responsive or includes a magnetically responsive particle. In some embodiments, the magnetically responsive particle is superpararmagnetic iron oxide (SPION).

In some embodiments, the second agent may be comprised in the same or different nanoparticle from the agent that decreases expression of a gene in a tissue of the inner ear.

Aspects of the disclosure relate to methods of applying the composition or agent that decreases expression of a gene in a tissue of the inner ear and the second agent in a therapeutically effective amount sufficient to treat hearing loss and/or restore and/or regenerate hair cells. In some embodiments, the applying steps are carried out simultaneously. In alternate embodiments, the applying steps are carried out sequentially. In further embodiments, the second agent is applied before or after the composition or agent that decreases expression of a gene in a tissue of the inner ear is applied.

BRIEF DESCRIPTION OF THE DRAWINGS

The patent or application file contains drawings executed in color. Copies of this patent or patent application publication with color drawing(s) will be provided by the Office upon request and payment of necessary fee.

FIGS. 1A-1D are labeled diagrams of the inner ear.

DETAILED DESCRIPTION

1. Definitions

Figure 2:
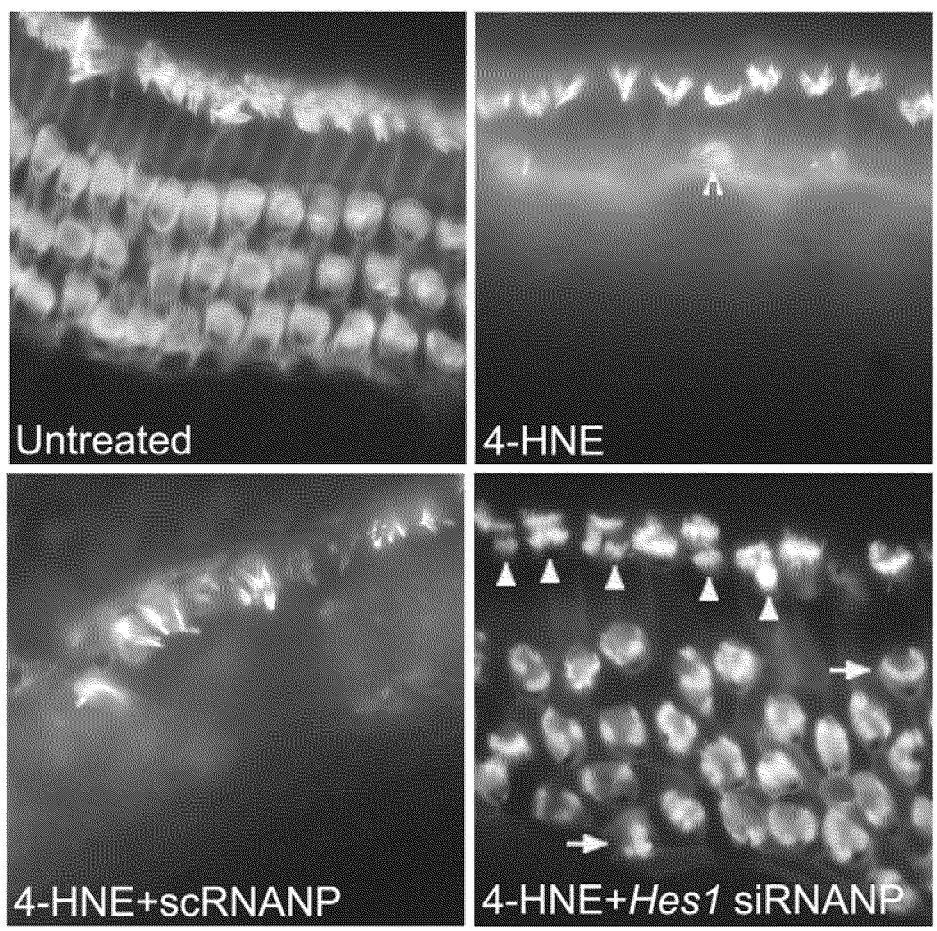
FIG. 2 depicts representative images from the middle turn of murine organs of Corti (OCs) in an experiment used to demonstrate that Hes1 siRNA-loaded PLGA nanoparticle (NP) treatment regenerates hair cells (HC)s following an ototoxic insult. Neonatal (P3) murine OCs were exposed to the ototoxin, 4-hydroxyl-2-nonenal (4-HNE, 450 μM), for 24 h and then either left untreated or were treated with either non-targeting scrambled RNA NPs (scRNANP) or Hes1 siRNA-loaded NPs (Hes1 siRNANP), and after 7 days, tissues were fixed and labeled with fluorophore-conjugated phalloidin. Three rows of outer hair cells (OHCs) and one row of inner hair cells (IHCs) were observed in OCs from the untreated cultures (upper left panel) and one row of IHCs and few, dispersed OHCs (open arrowheads) were observed in 4-HNE treated (upper right panel) and 4-HNE plus scRNANP-treated OCs (lower left panel). Extra OHCs (arrows, lower right panel)) and IHCs (arrowheads, lower right panel) were observed in OCs treated with Hes1 siRNANPs (800 μm/mL).

As used herein, the term "an amount sufficient to" refers to amount that enables the achievement of the intended effect, for example, to decrease the expression of a gene in a tissue of the inner ear. Such an amount may be determined through various assays known in the art based on the intended effect.

As used herein, the terms "applying" or "administering" refer to all means of introducing the specified agent, composition, or force to the specified region or subject. "Administration" or "application" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application. Administration can be for use in industrial as well as therapeutic applications.

As used herein, the term "biodegradable" is used herein to describe substances, such as polymers, compositions, and formulations, intended to degrade during use. Biodegradable substances may also be "biocompatible," i.e. not harmful to living tissue. Non-limiting exemplary biodegradable substances include poly(lactic acid) (PLA) and poly(lactic-co-glycolic) acid (PLGA), optionally pegylated.

As used herein, the term "BIO" or "6-bromoindirubin-3'-oxime" refers to a compound with the structure depicted below and pharmaceutically acceptable salts thereof:

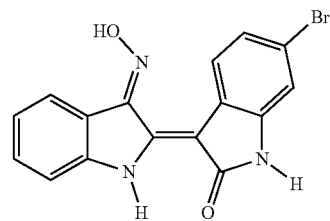 [SMILES: O=C1Nc2cc(Br)ccc2/C1=C1/Nc2ccccc2/C1=N\O]

As used herein, the term "cell" refers to a eukaryotic cell. The term "hair cells" refer to sensory epithelial cells characterized by having long cilia (e.g. stereocilia and/or kinocilia) which appear as fine hairs under microscopy; as used herein, hair cells (HCs) may be identified by their location—e.g. inner ear hair cells (IHCs) or outer ear hair cells (OHCs). Such hair cells are known to be present in at least the cochlear organ of Corti, maculae, and cristae of the ear.

As used herein, the term "differentiation" refers to the specific conditions that cause cells to develop into cells of a mature/specialized cell type (e.g. hair cells) that produce specific gene products which coincide with and/or promote/sustain the traits of the specified mature/specialized cell type.

As used herein, the term "expression" refers to the process by which polynucleotides are transcribed into mRNA and/or the process by which the transcribed mRNA is subsequently translated into peptides, polypeptides, or proteins. The expression level of a gene may be determined by measuring the amount of mRNA or protein in a cell or tissue sample; further, the expression level of multiple genes can be determined to establish an expression profile for a particular sample. When used in context of expression, the term "increase" refers to one or more actions that would serve to increase the amount of transcription and/or translation. Similarly, the term "decrease" refers to one or more actions that would serve to decrease the amount of transcription and/or translation.

As used herein, the term "gene" as used herein is meant to broadly include any nucleic acid sequence transcribed into an RNA molecule, whether the RNA is coding (e.g., mRNA) or non-coding (e.g., ncRNA).

As used herein, the term "GSK-3" refers to the protein associated with this name, namely a serine/threonine protein kinase that mediates the addition of phosphate molecules onto serine and threonine amino acid residues.

As used herein, the term "Hes1" (also known as Hes Family BHLH Transcription Factor 1, Class B Basic Helix-Loop-Helix Protein 39, Hairy-Like Protein, Hairy Homolog, BHLHb39, HHL, HRY, Hairy And Enhancer Of Split 1, (Drosophila), Hairy And Enhancer Of Split 1, Hairy Homolog (Drosophila), HES-1, or HL) refers to the gene and resulting protein product associated with this name and/or GCID: GC03P194136, HGNC: 5192, Entrez Gene: 3280, Ensembl: ENSG00000114315, OMIM: 139605, UniProtKB: Q14469 (each of which is incorporated by reference in its entirety herein), as well as homologs or orthologs thereof in a particular species—including, but not limited to, humans, mice, rats, guinea pigs, and chinchillas. A non-limiting exemplary amino acid sequence of human Hes1 is provided herein below (SEQ ID NO: 25):

```
MPADIMEKNSSSPVAATPASVNTTPDKPKTASEHRKSSKPIMEKRRRARI

NESLSQLKTLILDALKKDSSRHSKLEKADILEMTVKHLRNLQRAQMTAAL

STDPSVLGKYRAGFSECMNEVTRFLSTCEGVNTEVRTRLLGHLANCMTQI

NAMTYPGQPHPALQAPPPPPPGPGGPQHAPFAPPPPLVPIPGGAAPPPGG

APCKLGSQAGEAAKVFGGFQVVPAPDGQFAFLIPNGAFAHSGPVIPVYTS

NSGTSVGPNAVSPSSGPSLTADSMWRPWRN
```

As used herein, the term "Hes5" (also known as Hes Family BHLH Transcription Factor 5, Class B Basic Helix-Loop-Helix Protein 38, Hairy And Enhancer Of Split 5, BHLHb38, Hairy And Enhancer Of Split 5 (Drosophila)) refers to the gene and resulting protein product associated with this name and/or GCID:GC01M002528, HGNC: 19764, Entrez Gene: 388585, Ensembl: ENSG00000197921, OMIM: 607348, UniProtKB: Q5TA89 (each of which is incorporated by reference in its entirety herein), as well as homologs or orthologs thereof in a particular species—including, but not limited to, humans, mice, rats, guinea pigs, and chinchillas. A non-limiting exemplary amino acid sequence of human Hes5 is provided herein below (SEQ ID NO: 26):

```
MAPSTVAVELLSPKEKNRLRKPVVEKMRRDRINSSIEQLKLLLEQEFARH

QPNSKLEKADILEMAVSYLKHSKAFVAAAGPKSLHQDYSEGYSWCLQEAV

QFLTLHAASDTQMKLLYHFQRPPAAPAAPAKEPKAPGAAPPPALSAKATA

AAAAAHQPACGLWRPW
```

As used herein, the term "inhibitor" refers to a composition or agent that represses or prevents a molecule (e.g. a protein, nucleic acid, or other biological molecule) from engaging in a particular reaction. For example, a GSK-3 inhibitor may be used to refer a composition or agent that prevents GSK-3 in engaging in one or more of its biological functions. Non-limiting exemplary GSK-3 inhibitors include BIO, TIDE, Chiron compounds, lithium chloride, and SB-216763.

As used herein, the term "MAPK1" (also known as Mitogen-Activated Protein Kinase 1, Extracellular Signal-Regulated Kinase 2, Mitogen-Activated Protein Kinase 2, MAP Kinase Isoform P42, MAP Kinase 1, MAP Kinase 2, EC 2.7.11.24, P42-MAPK, MAPK 2, PRKM1, PRKM2, ERK-2, ERK2, ERT1, Protein Tyrosine Kinase ERK2, EC 2.7.11, P42MAPK, P41mapk, MAPK 1, MAPK2, P40, P38, ERK, P41) refers to the gene and resulting protein product associated with this name and/or GCID: GC22M021754, HGNC: 6871, Entrez Gene: 5594, Ensembl: ENSG00000100030, OMIM: 176948, UniProtKB: P28482 (each of which is incorporated by reference in its entirety herein), as well as homologs or orthologs thereof in a particular species—including, but not limited to, humans, mice, rats, guinea pigs, and chinchillas. A non-limiting exemplary amino acid sequence of human MAPK1 (isoform 1) is provided herein below (SEQ ID NO: 27):

```
MAAAAAAGAGPEMVRGQVFDVGPRYTNLSYIGEGAYGMVCSAYDNVNKVR

VAIKKISPFEHQTYCQRTLREIKILLRFRHENIIGINDIIRAPTIEQMKD

VYIVQDLMETDLYKLLKTQHLSNDHICYFLYQILRGLKYIHSANVLHRDL

KPSNLLLNTTCDLKICDFGLARVADPDHDHTGFLTEYVATRWYRAPEIML

NSKGYTKSIDIWSVGCILAEMLSNRPIFPGKHYLDQLNHILGILGSPSQE

DLNCIINLKARNYLLSLPHKNKVPWNRLFPNADSKALDLLDKMLTFNPHK

RIEVEQALAHPYLEQYYDPSDEPIAEAPFKFDMELDDLPKEKLKELIFEE

TARFQPGYRS
```

As used herein, the term "magnetically responsive" refers to the capacity of a particle or agent to respond to an attractive or repellant force resulting from the physical phenomena known as magnetism. In some embodiments, being magnetically responsive permits controlled movement or transport of a particle or agent by application of a magnetic gradient. A non-limiting example of a "magnetically responsive" agent is iron oxide; certain iron oxide particles may be superparamagnetic. Such superparamagnetic iron oxide particles may be macro-scale, micro-scale, or nano-scale. Nano-scale superparamagnetic iron oxide particles are referred to by the shorthand SPION.

As used herein, the term "microspheres" includes substantially spherical colloidal structures, e.g., formed from biocompatible polymers such as subject compositions, having a size ranging from about one to about 1000 microns. In general, "microcapsules" may be distinguished from microspheres, because microcapsules are generally covered by a substance of some type, such as a polymeric formulation. The term "microparticles" is microspheres and microcapsules, as well as structures that may not be readily placed into either of the above two categories, all with dimensions on average of less than about 1000 microns. If the structures are less than about one micron in diameter, then the corresponding art-recognized terms "nanosphere," "nanocapsule," and "nanoparticle" may be utilized.

The term "pharmaceutically acceptable carrier" (or "pharmaceutically acceptable excipient") refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, microspheres, microparticles, or nanoparticles (comprising e.g., biodegradable polymers such as Poly(Lactic Acid-co-Glycolic Acid)), and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

As used herein, the term "plasticity" refers to the ability of one cell (e.g. stem cell) to take on characteristics of another cell and is generally used in context of differentiation. The term "pluripotent" refers to the ability of a cell to give rise to several different cell types.

As used herein, the term "polymer" refers to a molecule composed of repeating subunits. Generally, polymers have a tendency to have larger molecular mass relative to those molecules classified as "small molecule compounds."

As used herein the terms "replacing" or "regenerating" refer to the renewal, regrowth, or restoration of hair cells. The term "protecting" intends the prevention or mitigation of hair cell loss.

As used herein, the term "subject" of diagnosis or treatment is a cell or an animal such as a mammal, or a human. Non-human animals subject to diagnosis or treatment and are those subject to a named disease or condition (e.g. hearing loss) or animal models thereof, for example, simians, murines, such as, rats, mice, chinchilla, canine, such as dogs, leporids, such as rabbits, livestock, sport animals, and pets As used herein, the term "siRNA" intends a double-stranded RNA molecule that interferes with the expression of a specific gene or genes post-transcription. In some embodiments, the siRNA functions to interfere with or inhibit gene expression using the RNA interference pathway. Similar interfering or inhibiting effects may be achieved with one or more of short hairpin RNA (shRNA), microRNA (mRNA) and/or nucleic acids (such as siRNA, shRNA, or miRNA) comprising one or more modified nucleic acid residue—e.g. peptide nucleic acids (PNA), locked nucleic acids (LNA), unlocked nucleic acids (UNA), or triazole-linked DNA.

As used herein, the term "TIDE" or "tideglusib" refers to a compound with the structure depicted below and pharmaceutically acceptable salts and derivatives thereof:

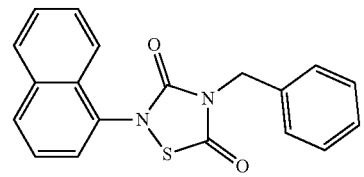 [SMILES: O=c1sn(-c2cccc3ccccc23)c(=O)n1Cc1ccccc1]

Non-limiting examples of the derivatives contemplated include those disclosed in US 2014/005195, which is incorporated by reference in its entirety herein. Such TIDE derivatives may have the same function as TIDE but be modified for improved stability, solubility, or pharmacokinetics. Further non-limiting examples of derivatives contemplated herein include those disclosed in Morales-Garcia et al. (2012) ACS Chem. Nuerosci. 3:963-917, which is incorporated by reference in its entirety herein. GSK3 inhibitors and derivatives thereof related to TIDE include the TDZD family of GSK3 inhibitor analogs.

As used herein, the term "tissue" refers to tissue of a living or deceased organism or any tissue derived from or designed to mimic a living or deceased organism As used herein, the term "therapeutically effective amount" refers to a quantity sufficient to achieve a desired effect. In the context of therapeutic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in breaking down a biofilm. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors. In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

As used herein, the term "treating" or "treatment" includes preventing a disease, disorder or condition from occurring in a subject predisposed to or having a disease, disorder and/or condition; inhibiting the disease, disorder or condition, e.g., impeding its progress; and relieving or reversing the disease, disorder, or condition, e.g., causing regression of the disease, disorder and/or condition. Treating a disease or condition may also include ameliorating at least one symptom of the particular disease or condition. The term "hearing loss" refers to impairment in the ability to apprehend sound; thus, treatment thereof implies any one of the above listed effects on the ability to apprehend sound. The term "sensorineural hearing loss" refers to a specific type of hearing loss where there is damage to the inner ear or to the nerve pathways from the inner ear to the brain.

2. Modes of Carrying Out the Disclosure

Aspects of the disclosure relate to methods of treating hearing loss, optionally sensorineural hearing loss, and/or replacing, regenerating, or protecting hair cells through the application of one or more agents or compositions to a specified tissue or area of the ear.

Areas of the ear that may be treated based on the methods disclosed herein include but are not limited to the outer, middle, or inner ear regions thereof which are labeled in FIG. 1.

Compositions

Aspects of the disclosure relate to a composition or an agent that decreases expression of a gene in a tissue of the inner ear and a second agent.

In some embodiments, the composition or agent that decreases expression of a gene in a tissue of the inner ear is an interfering nucleic acid, such as siRNA, shRNA, miRNA, antisense oligonucleotides (ASOs), and/or a nucleic acid comprising one or more modified nucleic acid residues. In some embodiments, the interfering nucleic acid is optimized (based on sequence) or chemically modified to minimize degradation prior to and/or upon delivery to the tissue of interest. Commercially available sources for these interfering nucleic acids include, but are not limited to, Thermo-Fisher Scientific/Ambion, Origene, Qiagen, Dharmacon, and Santa Cruz Biotechnology. In some embodiments, such optimizations and/or modifications may be made to assure that sufficient payload of the interfering nucleic acid is delivered to the tissue of interest. Other embodiments include the use of small molecules, aptamers, or oligonucleotides designed to decrease the expression of a gene by either binding to a gene's DNA to limit expression, e.g. antigene oligonucleotides, or impose post-transcriptional gene silencing (PTGS) through mechanisms that include, but are not limited to, binding directly to the targeted transcript or gene product or one or more other proteins in such a way that said gene's expression is reduced; or the use of other small molecule decoys that reduce the specific gene's expression. In some embodiments, the composition or agent that decreases expression of a gene in a tissue of the inner ear may include an inhibitor of the pathway by which the gene is regulated, e.g. a Notch signaling pathway inhibitor such as gamma secretase inhibitor (since transcription of, for example, Hes1 is mediated by Notch signaling).

In some embodiments, the gene is Hes1, Hes5, or MAPK1. Non-limiting exemplary sequences of these genes and siRNA sequences against them are provided in, for example, U.S. Pat. No. 9,101,647, the entirety of which is incorporated herein by reference in its entirety. Further non-limiting exemplary siRNA sequences are provided herein below, as SEQ ID NOs: 1-24 (the lower case letters in these sequences being optional; SEQ ID NO: 1-14, directed to Hes1; SEQ ID NO: 15-20, directed to Hes5; SEQ ID NO: 21-24, directed to MAPK1). Additional sequences may be determined according to methods known in the art, e.g. Fakhr et al. (2016) Cancer Gene Ther. 23(4):73-82.

| | Location (nt #) | Passenger strand | Guide strand |
|---|---|---|---|
| RNAi Target Sequences for Murine Hes1 mRNA (accession # NM_008235.2; ORF: 235-1083) | | | |
| Molecule 1* | 239-257 (within ORF) (amino acids 2-8) | 5' CAGCUGAUAUA AUGGAGAAtt 3' (SEQ ID NO: 1) | 3' ttGUCGACUAU AUUACCUCUU 5' (SEQ ID NO: 2) |
| Molecule 2 | 371-389 (within ORF) (amino acids 46-52) | 5' GAAGGGCAAGA AUAAAUGAtt 3' (SEQ ID NO: 3) | 3' ttCUUCCCGUU CUUAUUUACU 5' (SEQ ID NO: 4) |
| Molecule 3* | 1363-1381 (3' UTR) | 5' GAUGCCAAAGA UGUUUGAAtt 3' (SEQ ID NO: 5) | 3' ttCUACGGUUU CUACAAACUU 5' (SEQ ID NO: 6) |
| RNAi Target Sequences for Human Hes1 mRNA (accession # NM_005524.3, ORF: 240-1082) | | | |
| Molecule 4 | 302-320 (within ORF) (amino acids 21-27) | 5' CAACACGACAC CGGAUAAAtt 3' (SEQ ID NO: 7) | 3' ttGUUGUGCUG UGGCCUAUUU 5' (SEQ ID NO: 8) |
| Molecule 5* | 1299-1317 (3' UTR) | 5' GGAUUGCGCCU UUGUAUUAtt 3' (SEQ ID NO: 9) | 3' ttCCUAACGCG GAAACAUAAU 5' (SEQ ID NO: 10) |
| Molecule 6 | 1323-1341 (3' UTR) | 5' GCUCAGAUGAC AUUUCGUUtt 3' (SEQ ID NO: 11) | 3' ttCGAGUCUAC UGUAAAGCAA 5' (SEQ ID NO: 12) |

-continued

|  | Location (nt #) | Passenger strand | Guide strand |
|---|---|---|---|
| Molecule 7* | 673-691 (within ORF) (amino acids 145-151) | 5' ACUGCAUGACC CAGAUCAA 3' (SEQ ID NO: 13) | 3' ttGACGUACUG GGUCUAGUU 5' (SEQ ID NO: 14) |

RNAi Target Sequences for Murine Hes5 mRNA
(accession # NM_010419.4, ORF: 74-577)

| Molecule 8 | 165-183 (within ORF) (amino acids 31-37) | 5' GCAUCAACAGC AGCAUAGAtt 3' (SEQ ID NO: 15) | 3' ttCGUAGUUGU CGUCGUAUCU 5' (SEQ ID NO: 16) |
|---|---|---|---|
| Molecule 9 | 726-744 (3' UTR) | 5' GGUCAUUCUUA GAGAAUGUtt 3' (SEQ ID NO: 17) | 3' ttCCAGUAAGA AUCUCUUACA 5' (SEQ ID NO: 18) |
| Molecule 10 | 1141-1159 (3' UTR) | 5' CGAUGAUCCUU AAAGGAUUtt 3' (SEQ ID NO: 19) | 3' ttGCUACUAGG AAUUUCCUAA 5' (SEQ ID NO: 20) |

RNAi Target Sequences for Murine MAPK1 mRNA
(accession # NM_011949.3, ORF: 246-1322)

| Molecule 11* | 1082-1100 (within ORF) (amino acids 279-285) | 5' UGCUGACUCCA AAGCUCUGtt 3' (SEQ ID NO: 21) | 3' ttACGACUGAG GUUUCGAGAC 5' (SEQ ID NO: 22) |
|---|---|---|---|
| Molecule 12 | 962-980 (within ORF) (amino acids 239-245) | 5' GGGUAUUCUUG GAUCUCCAtt 3' (SEQ ID NO: 23) | 3' GACCCAUAAGA ACCUAGAGGU 5' (SEQ ID NO: 24) |

*Molecules 1 and 3 have guide sequences that are complementary to conserved target sequences in mouse/human transcripts; the mRNA target sequence for Molecule 1 is conserved in mouse, rat, human, and guinea pig Hes1 transcripts.
*Molecules 5 and 7 have guide sequences that are complementary to conserved target sequences in mouse/human transcripts; the mRNA target sequences for Molecules 5 and 7 are conserved in mouse, rat, human, and guinea pig HES1 transcripts.
*Molecule 11 has guide sequences that are complementary to conserved target sequences in mouse/human transcripts; the mRNA target sequence for Molecule 11 is conserved in mouse, human, and guinea pig MAPK1 transcripts.
Amino acid positions correspond to codons that are either partially or fully incorporated within mRNA locus bound by guide strand.

In some embodiments, the second agent is a priming composition. In some embodiments, the priming composition exhibits one or more functions selected from the group consisting of stabilizing β catenin, increasing the number of pluripotent cells in the inner ear, increasing plasticity of pre-existing pluripotent cells in the inner ear, or signaling differentiation in cells of the inner ear. In some embodiments, this second agent is a GSK-3 inhibitor. In further embodiments, the GSK-3 inhibitor is either 6-bromoindiru-bin-3'-oxime (BIO) or tideglusib (TIDE). In some embodiments, the second agent may comprise one or more ingredients, such as, but not limited to, the GSK-3 inhibitor and/or one or more factors involved in developmental signaling (e.g. basic fibroblast growth factor (FGF2 and/or FGF mimetics); non-limiting examples of this family are provided in, for example Katoh and Katoh (2006) Cancer Biol. Therapy 5(9):1059-1064, which is incorporated by reference in its entirety herein.

Formulations

In some embodiments, the composition that decreases expression of a gene in a tissue of the inner ear may include a formulation and/or particles, which in turn may comprise an agent that decreases expression of a gene in a tissue of the inner ear.

Non-limiting examples of such formulations and/or particles include a nanoparticle, lipofection, gel or hydrogel (e.g. Kechai et al. (2016) J Control Release. 226:248-57), nanoemulsion (e.g. U.S. Publication No. 2005/0288292), microparticle (e.g. Yang et al. (2012) Electrophoresis. 33(21):3173-80), colloidal suspension (e.g. Ariana et al. (2016) Otolaryngol Head Neck Surg. 154(5):917-9), sterile suspension (e.g. Ciprodex at www.ciprodex.com/), solution (e.g. Parra et al. (2002) Antimicrob Agents Chemother. 46(3):859-62.), aerosol (e.g. Li et al. (2013) IEEE Trans. Biomed. Eng. 60(9):2450-2460), powder (e.g. fauquier-ent.blogspot.com/2009/10/treatment-of-chronic-draining-ear.html#ixzz459wcRKOr), eardrop (e.g. Winterstein et al. (2013) Otolaryngol Head Neck Surg. 148(2):277-83), nanofiber (e.g. Akiyama et al. (2013) Int J Nanomedicine. 8: 2629-2640), or cream (e.g. Quadiderm® cream). All references cited herein above are incorporated by reference in their entirety.

In some embodiments, the formulations and/or particles are specifically adapted for delivery to the inner ear. For example, a gel formulation such as a thermo-reversible hydrogel (e.g. Pluronic F-127) allows for drugs to be maintained in the middle ear, in-contact with the round window membrane, such that the drug could diffuse or be transported into the inner ear. A colloidal suspension could likewise be formulated specifically for injection directly into the inner ear or across the tympanic membrane for diffusion or other means of transport through the round window membrane. Likewise, a nanoparticle or formulation comprising a plurality of nanoparticles can be formulated for controlled delivery, by way, for example, of magnetic force. Such a method can be generalized to microparticles and/or alternate nanoscale structures.

In some embodiments, the second agent may be comprised in the same or different formulation and/or particle from the agent that decreases expression of a gene in a tissue of the inner ear. In some embodiments, the second agent is in the same or different formulation and/or to facilitate the timing of its application to the target tissue—simultaneous or sequential relative to the particle the agent that decreases expression of a gene in the tissue of the inner ear. For example, for simultaneous delivery but sequential release, the second agent may be comprised in a solution that is administered along with a sustained release formulation and/or particle comprising the agent that decreases expression of a gene in the tissue of the inner ear. A similar effect may be achieved through the use of a single formulation and/or particle comprising both agents formulated for different release profiles for the different agents.

In some embodiments, a nanoparticle comprises or encapsulates an agent that decreases expression of a gene in a tissue of the inner ear. In some embodiments, the nanoparticle comprises a biodegradable polymer. In further embodiments, the biodegradable polymer is poly(lactic-co-glycolic acid) (PLGA) or pegylated PLGA (PEG-PLGA). In some embodiments, the nanoparticles may include further additives, including but not limited to polyvinyl alcohol (PVA) or other known nanoparticle stabilizers. In some embodiments, the nanoparticle is magnetically responsive or includes a magnetically responsive particle. In some embodiments, the magnetically responsive particle is iron oxide, optionally superpararmagnetic iron oxide (SPION). In some embodiments, the nanoparticle may be further comprised in a solution, suspension, gel, or other formulation suitable for its delivery.

In further embodiments, the same or a different nanoparticle may comprise or encapsulate the second agent. The nanoparticles disclosed herein above can be formed through water-in-oil emulsion or any other technique known in the art. Thus, a variety of options are available for generating nanoparticles comprising more than one agent, such as, but not limited to, dual core/shell loading (e.g. Narayan et al. (2014) Acta Biomaterialia. 2112-2124), co-encapsulation (e.g. Song et al. (2008) Eur J Pharm Biopharm. 69(2):445-53.), and layer by layer deposition (e.g. Deng et al. (2013) ACS Nano. 7(11):9571-9584). All references cited herein above are incorporated by reference in their entirety.

The nanoparticles may be formulated to facilitate timing of release, for example, a poorly water soluble second agent (e.g. TIDE) could be encapsulated in the organic shell of a nanoparticle loaded with the hydrophilic agent that decreases expression of a gene in the tissue of the inner ear (e.g. siHes1). As the second agent will be more accessible to water, it will be released first, followed by the sustained release of the agent that decreases expression of a gene in the tissue of the inner ear.

Modes of Administration

The above disclosed agents, compositions, formulations, and/or particles can be administered simultaneously or sequentially—with the second agent being administered before or after the agent that decreases expression of a gene in the tissue of the inner ear.

Dosing may be readily determined through methods known in the art. For example, an effective in vitro dose, e.g. between about 0.5 to 10 µM of the second agent (e.g. TIDE) and between about 20 to 320 nM of the agent that decreases expression of a gene in the tissue of the inner ear (e.g. siHes1), may be scaled up to the appropriate in vivo dose. A non-limiting exemplary in vivo dose of an agent that decreases expression of a gene in the tissue of the inner ear is between about 100 to 300 nM siHes1. In some embodiments, appropriate in vivo doses may be an amount between about 5 nM to 5 mM of the second agent (e.g. TIDE) and between about 1 nM to 5 mM of the agent that decreases expression of a gene in the tissue of the inner ear (e.g. siHes1). It is contemplated that an appropriate dose regiment may require one or more doses at appropriate intervals for each agent; these intervals may vary by agent or indication. Appropriate dosing intervals may be about one day, two days, three days, four days, five days, six days, one week, two weeks, three weeks, four weeks, five weeks, one month, two months, three months, or more.

In some embodiments, application and/or administration may be, for example, direct application, injection, or infusion of a specified agent or composition. In some embodiments, the specified agent or composition can be administered by direct injection through the round window membrane (RWM) or by infusion through a temporary or permanent cannula placed through the RWM. In some embodiments, the infusion or injection can be assisted through an attached microinfusion pump, dialysis apparatus, or fluid exchange system. In similar embodiments, injection or infusion technology could also be applied to the oval window, and/or the oval window ligament or annulus. The injections or infusion could further be accomplished through a cochleostomy or other opening into the boney labyrinth, such as one of the semicircular canals. Alternatively, the cortical bone could be removed over the labyrinth, and the specified agent or composition could be applied over the decorticated bone for intraosseous delivery. In some embodiments, the composition or agent is delivered systemically through intravenous or intraarterial administration.

The above listed routes of administration are by no means exhaustive. In general, there are a variety of means of delivery to the inner ear—that fall into two general categories: through an ostomy into the inner ear (where necessary, opened by drill, knife, or laser) and through diffusion through the RWM, the ligament of the stapes footplate or through an area of cochlear, or vestibular structure (typically where a region of bone was thinned to a thickness so that there is only the very thinnest of bone remaining separating the middle ear space form the inner ear endosteal lining and fluid).

In some embodiments, where an ostomy is used, the ostomy is conducted by machine or by hand. In some embodiments, the ostomy is through the footplate of the stapes, through an opening drilled into the cochlea, through an opening drilled into the semicircular canal, through the vestibular aqueduct, through a cochleostomy, through a direct opening into the RWM. In some embodiments, the ostomy is made for the insertion of an implant electrode; thus, one or more of the disclosed formulations, and/or particles may be bonded to the electrode surface to elute the one or more agents or compositions into the environment. In some embodiments, one or more openings subject to ostomy may be accessible for between about one day to about one week, two weeks, three weeks, four weeks, or a month, e.g. between about 1 to 30 days. In some embodiments, the ostomy is suited for a single injection or continuous infusion over the duration that the opening is accessible.

In some embodiments, where diffusion is employed, the agents, compositions, formulations, and/or particles allow diffusion across a particular membranous structure into the inner ear fluids. Non-limiting exemplary formulations include solution, gel, emulsion, or suspension. For example, a gel or pellet may be suited for the delivery of one or more agents, compositions, and/or particles disclosed herein above. A gel, for instance, may be placed transtympanically over the stapes and over the RWM and over the area of thinned bone to enhance delivery by increasing the surface area for delivery. Similarly, a solid or semi-solid pellet may be placed onto the stapes footplate, RWM or area of thinned bone as a means of enhancing drug contact with said membranes and keeping the drug from being removed from the middle ear space.

Not to be bound by theory, one of the challenges of a less invasive diffusion approach to delivering drugs to the inner ear fluids may be the small surface area of the RWM and the even smaller surface area of the ligament of the stapes footplate. In some embodiments, a procedure known in the art as "blue-lining" may resolve this issue. By "blue-lining," the drilled-out area is extremely thinned out and just barely covers the endosteal membrane on the inner surface of the inner ear. This may greatly increase the surface area for absorption and may be less invasive than making an actual opening into the cochlea or other region of the inner ear. A skilled ear surgeon should be able to perform this procedure safely.

In some embodiments, delivery may be achieved in single or multiple injections across the tympanic membrane. In some embodiments, delivery may be achieved through single or multiple injections through a plastic tube inserted into the tympanic membrane. In some embodiments, delivery may be achieved through continuous infusion through a catheter, wherein its tip is placed directly on the area where diffusion is to occur.

Kits

Kits containing the agents and instructions necessary to perform the in vitro and in vivo methods as described herein also are claimed. Accordingly, the disclosure provides kits for performing these methods, which may include one or more agents, compositions, formulations, and/or particles disclosed herein as well as instructions for carrying out the methods disclosed herein, such as collecting tissue and/or performing the screen, and/or analyzing the results, and/or administration of an effective amount of an interfering agent as defined herein. These can be used alone or in combination with other suitable therapeutic agents.

Indications

In some embodiments, the formulations, compositions, methods, modes of administration, and kits disclosed herein may be used in the treatment of one or more indications. Non-limiting exemplary indications contemplated herein include sensorineural hearing loss resulting in loss of cochlear sensory hair cells resulting from loud noise, acoustic trauma, explosive blast, toxins, viral or bacterial infection, aging, genetic hearing loss involving the loss of sensory hair cells and metabolic conditions such as diabetes mellitus or hypothyroidism. Further non-limiting exemplary indications include balance disorders due to the loss or damage of sensory hair cells in the peripheral vestibular organ (cristae or maculae) due to toxins, trauma, viral or bacterial infection, aging, genetically induced balance sensory hair cell loss or metabolic conditions such as diabetes mellitus or hypothyroidism.

3. EXAMPLES

The following examples are non-limiting and illustrative of procedures which can be used in various instances in carrying the disclosure into effect. Additionally, all reference disclosed herein below are incorporated by reference in their entirety.

Example 1-Generation of siHes1 Nanoparticles and Assessment Thereof

Generation of Loaded Nanoparticles

The siRNA-loaded PLGA nanoparticles prepared for this study were formulated by the water-in-oil-in-water (w1/o/w2) double emulsion solvent evaporation method as previously reported (Cun et al. (2010) Intl. J. Pharmaceutics 390:70-75; Du et al. (2013) Hear. Res. 304C:91-110). Briefly, siRNA was dissolved in 50 µL of TE buffer (10 mM Tris—HCl and 1 mM EDTA in MilliQ water, pH 7.5) and was mixed with 100 mL dichloromethane (DCM) containing 100 mg of PLGA, and the mixture was emulsified by sonication into a primary w1/o emulsion. Four milliliters of 5% (w/v) polyvinyl alcohol (PVA) in MilliQ water was poured directly into the primary emulsion prior to further emulsification by sonication for 30 sec×3 to form a w1/o/w2 double emulsion. The resulting emulsion was diluted with 50 mL of 0.3% (w/v) PVA in MilliQ water and stirred magnetically for 2 h at room temperature to evaporate the DCM. The PLGA nanoparticles were collected by ultracentrifugation at 13,000× g for 20 min at 4° C., washed thrice with MilliQ water, resuspended in 5 mL of MilliQ water, and freeze-dried (at −100° C. and under 40 mTorr). The optimum formula of siRNA-loaded NPs was made from 15 nmol of siRNA, 100 mg of PLGA, and 5% PVA. The resulting NPs were characterized for particle mean diameter (PMD), polydispersity index (PDI), percent drug encapsulation efficiency (EE %), and morphology, using dynamic light scattering (Zetasizer Nano ZS, Malvern, Instruments Ltd, Worcestershire, UK), UV-Vis Spectrophotometer (nanoDrop 2000, Thermo Scientific, Waltham, Mass.), and scanning electron microscopy (Zeiss Supra 55, VP, FE-SEM, Oberkochen, Germany), respectively. The synthesized NPs are generally stored at −80° C. until time of use.

In Vitro Nanoparticle Studies

Neonatal (P3) murine organs of Corti (OCs) were exposed to the ototoxin, 4-hydroxyl-2-nonenal (4-HNE, 450 µM) for 24 h and then either left untreated or were treated with either non-targeting scrambled RNA NPs (scRNANP) or Hes1 siRNA-loaded PLGA NPs (Hes1 siRNANP), and after 7 days, tissues were fixed and labeled with fluorophore-conjugated phalloidin (FIG. 2).

Figure 3:
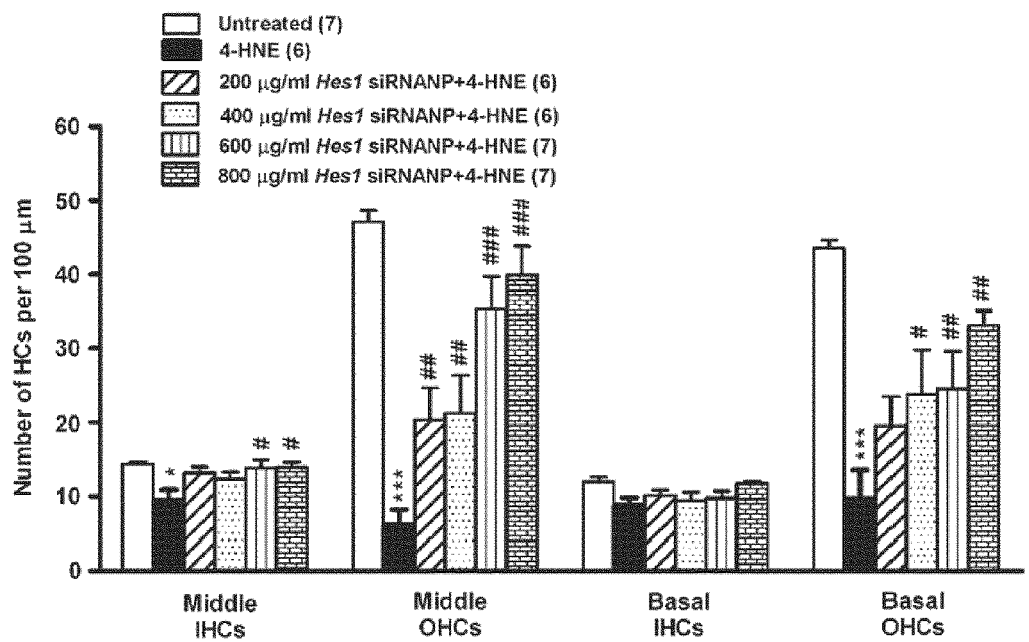
FIG. 3 demonstrates a dose-dependent response that was observed in the number of HCs restored in neonatal murine OCs exposed to the ototoxin, 4-HNE, in response to Hes1 siRNA NP treatment. Treatment with a high dose of NPs (>400 μg/mL) resulted in a significant increase in OHC numbers in the basal turn as well. *** and * indicate $p<0.001$ and 0.05, respectively, compared to untreated cultures. ###, ## and # indicate $p<0.001$, 0.01 and 0.05, respectively, compared to the group exposed to 4-HNE alone. Numbers in brackets indicate the number of OCs in which HCs were counted.
Figure 4:
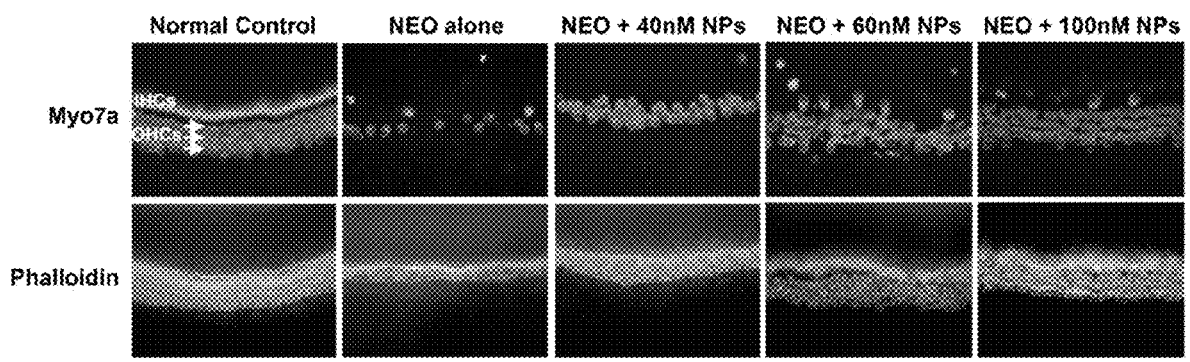
FIG. 4 depicts representative images from the middle turn of OCs in the following experiment. Neonatal (P3) murine OCs were exposed to the ototoxic aminoglycoside, neomycin (NEO, 0.75 mM), for 24 h and then either left untreated or were treated with escalating doses of Hes1 siRNA-loaded NPs. After 7 days, tissues were fixed and labeled with a Myo7a antibody (green, upper panel) and fluorophore-conjugated phalloidin (lower panel). Three rows of OHCs and one row of IHCs were observed in OCs from the untreated cultures (upper left panel). Few, dispersed OHCs (open arrowheads) were observed in untreated, NEO-exposed OCs (NEO alone). Dose-dependent increases in HC numbers were observed in OCs treated with escalating doses of siHes1-encapsulated PLGA NPs. Dose equivalents of NPs shown correspond to total siRNA concentrations in solution and represent 145, 230, and 385 μg/mL siHes1-encapsulated PLGA NPs, respectively.
Figure 5:
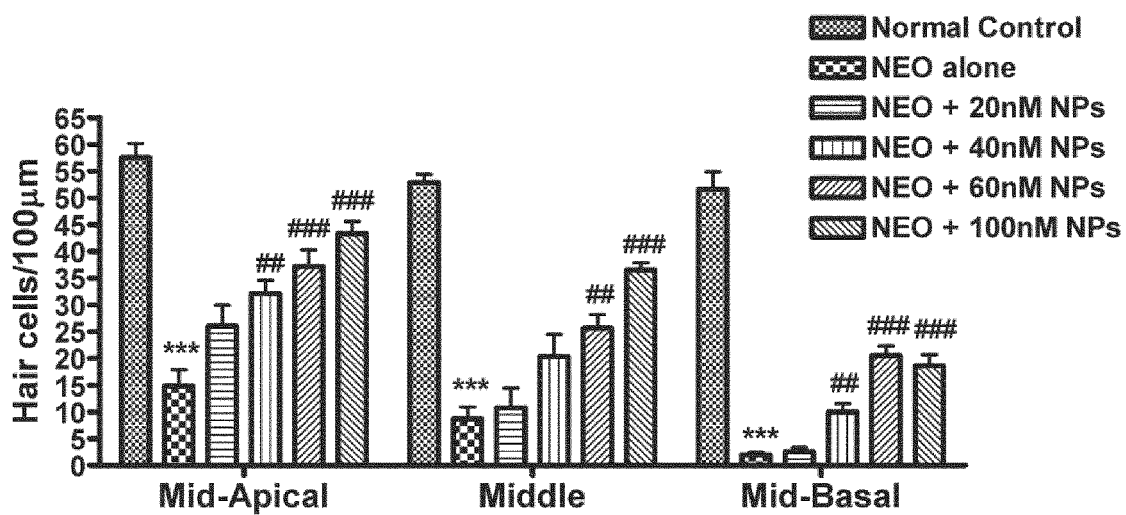
FIG. 5 demonstrates that a dose-dependent response was also observed in the number of HCs (Myo7A-positive cells) restored in neonatal murine OCs exposed to the ototoxic aminoglycoside, neomycin (NEO), and subsequently treated with escalating doses of Hes1 siRNA NPs. HC counts were performed across the mid-apical, middle, and mid-basal turns of the OCs. Dose equivalents shown represent total siRNA concentrations in solution and correspond to 78, 145, 230, and 385 μg/mL PLGA NPs. Significant increases in HC numbers were observed. *** indicate $p<0.001$, compared to untreated cultures. ### and ## indicate $p<0.001$ and 0.01, respectively, compared to the group exposed to NEO alone.
Figure 6:
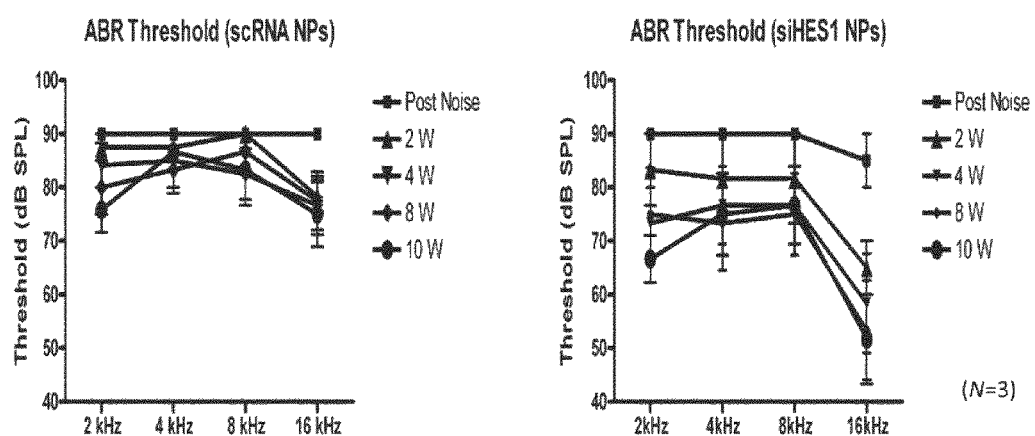
FIG. 6 depicts the time course of auditory brainstem response (ABR) threshold recovery (post-injury) in noise-damaged cochleae of live guinea pigs from sham-treated or therapeutic siHES1 NP-treated ears at test frequencies of 2, 4, 8, and 16 kHz. The acoustic trauma was induced by an acoustic overexposure of 130 dB SPL centered at 4 kHz for 2 h. Delayed (72h post-injury) therapeutic intervention with either sham non-targeting scrambled RNA (scRNA)—loaded NPs (800 μg/mL) or therapeutic siHES1 NPs (800 μg/mL) was conducted via unilateral-infusion directly into the basal turn of the cochlea (cochleostomy), using a mini-osmotic pump, which was surgically removed seven days later. ABR measurements were then conducted among animals from both experimental cohorts at two, four, eight, and ten weeks post-injury. In comparison to sham-treated controls, siHES1 NP-treated ears in noise-exposed animals exhibited a greater degree of progressive auditory functional restoration (i.e. reduced ABR thresholds across the tested frequency range) over the time course of this experiment
Figure 7:
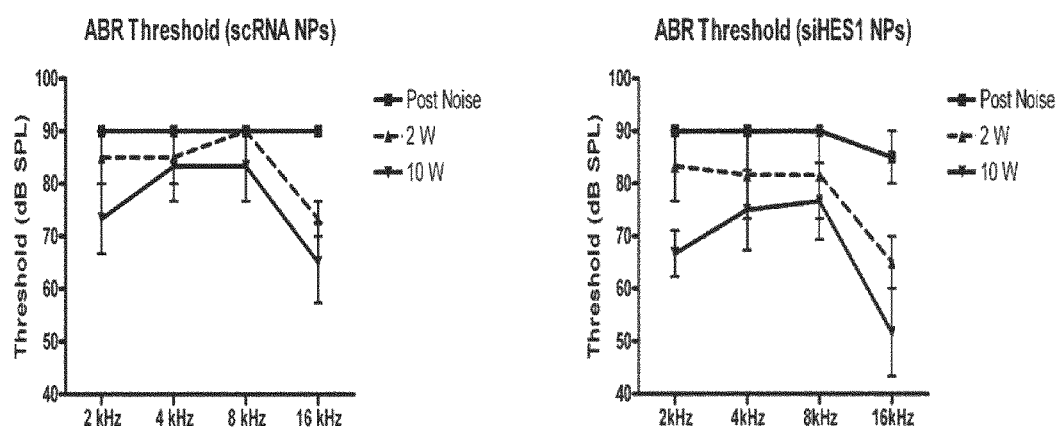
FIG. 7 depicts a simplified time course of the ABR threshold recovery portrayed in FIG. 6, demonstrating that the level of hearing recovery achieved following delayed (72 h post-injury) therapeutic intervention with siHES1 NPs in live guinea pigs exposed to an acute acoustic trauma was greater than that achieved with non-targeting scRNA NPs.
Figure 8:
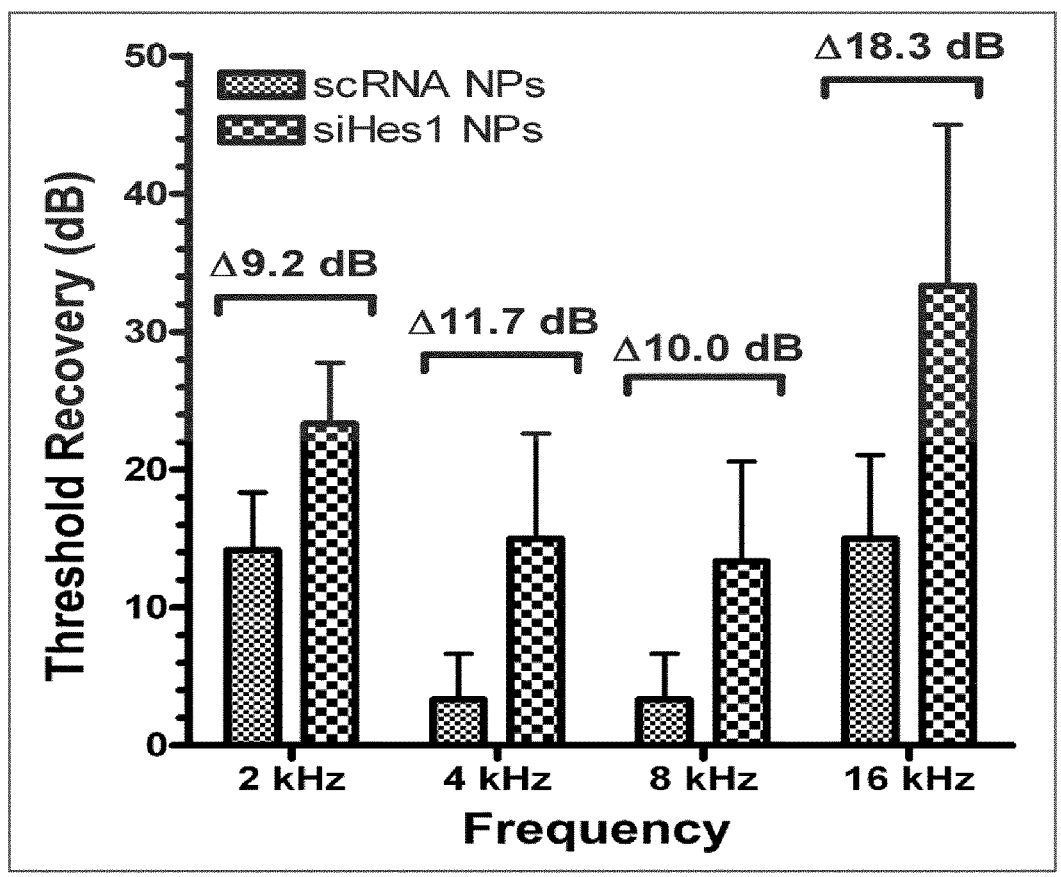
FIG. 8 shows differences in ABR threshold recovery in live guinea pigs post-AAT following delayed (72 h post-injury) therapeutic intervention with either scRNA NPs or siHES1 NPs in vivo in surgically-infused ears at ten weeks after treatment compared to one day after the acoustic overexposure at test frequencies of 2, 4, 8, and 16 kHz. The siHES1 NP treatment-specific improvement on threshold recovery observed here post-AAT would be expected to be clinically significant.

Alternatively, the experiment was conducted in the same manner as above, using the ototoxic aminoglycoside, neomycin (NEO, 0.75 mM), with subsequent therapeutic application of Hes1 siRNA-loaded PLGA NPs, tissue fixation, and affinity labeled with both an antibody against the hair cell marker, myosin VIIa (Myo7a) and fluorophore-conjugated phalloidin to facilitate immunofluorescence-mediated quantification of HCs along the length of the cochlear spiral (FIG. 4). A dose-dependent response was observed in the number of HCs restored in neonatal murine OCs exposed to either ototoxin (4-HNE or NEO) in response to Hes1 siRNA NP treatment (FIGS. 3 and 5).

In Vivo Nanoparticle Studies

Figure 9:
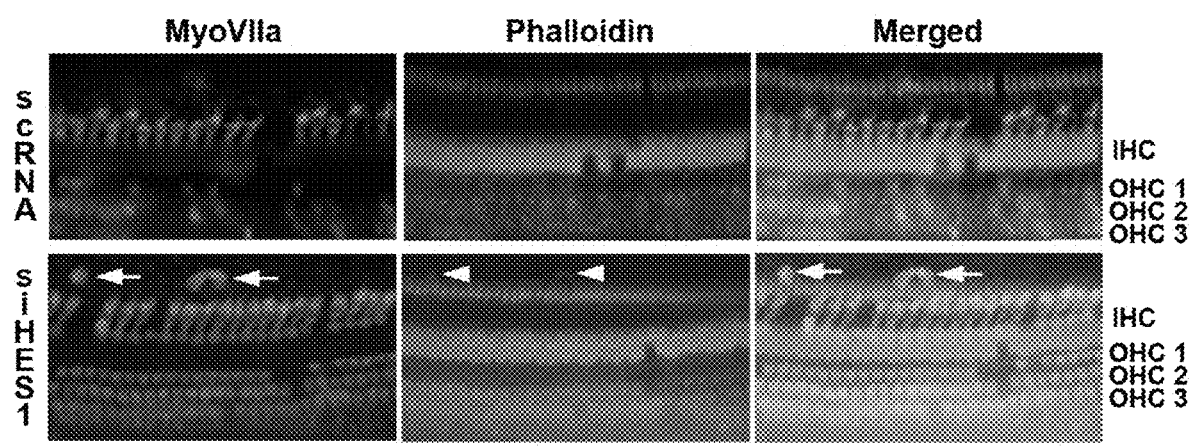
FIG. 9 depicts images collected from the basal turn of the cochlea from treated ears, which demonstrate that siHES1 NP infusion resulted in increased HC numbers in noise-damaged cochlea of mature pigmented guinea pigs. Myo7a- and Phalloidin-labeling in sham (scRNA)—and therapeutic (siHES1)—treated ears revealed pronounced loss of OHCs in scRNA NP-infused ears and marked restoration of OHC numbers in siHES1 NP-treated ears. Arrows denote the occurrence of supernumerary Myo7a-positive IHCs bearing stereociliary bundles (arrowheads) in the siHES1-treated ears
Figure 10:
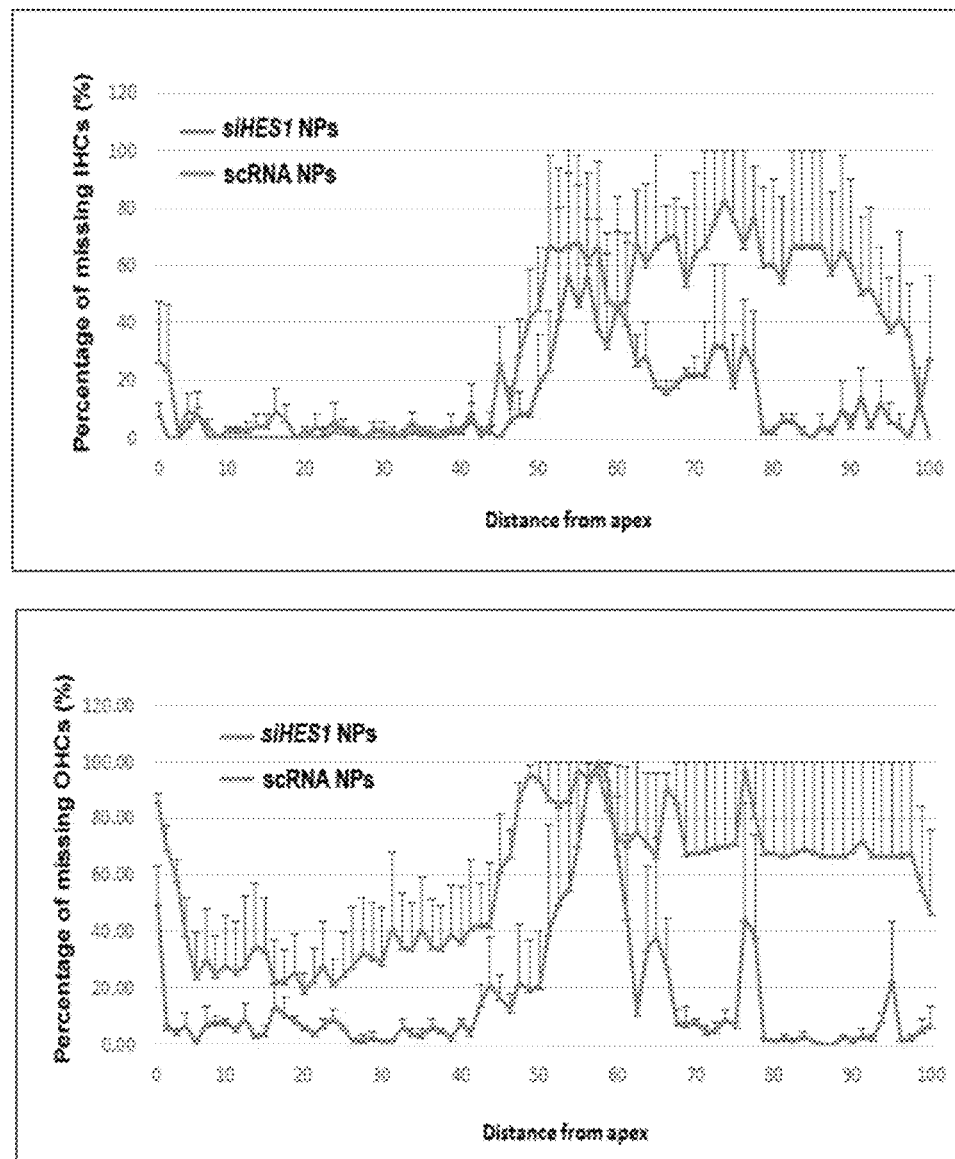
FIG. 10 shows that siHES1 NP treatment restores HC numbers in vivo following a damaging acoustic overexposure. The number of Myo7a-immunolabeled IHCs and OHCs were quantified and graphed as cytocochleograms depicting percent IHC and OHC loss as a function of percent distance (frequency place in kiloHertz) from the OC apex in scRNA NP- and siHES1 NP-treated ears at ten-weeks post-injury. The data are plotted as mean±SEM. Three cochleae were analyzed for each data point. A pronounced basal-to-apical gradient of OHC and IHC loss was observed in scRNA NP-treated ears, which was dramatically reduced across the entire length of the cochlear spiral in siHES1 NP-treated ears, including the high-frequency tonotopic region along the basal turn of the OC.

Adult pigmented guinea pigs (250 g, 4-wk-old) were exposed to an acoustic overexposure centered at 4 kHz at 130 dB SPL for two hours. Seventy-two (72) hours after the injury (i.e. a delayed treatment), mini-osmotic pumps loaded with 800 µg/mL of either non-targeting scrambled RNA NPs or siHES1 NPs were surgically implanted into the basal turn of the cochlea (cochleostomy), and the sham or therapeutic treatments were unilaterally-infused into the cochleae over the course of seven days, after which the pumps were surgically removed. Auditory brainstem response (ABR) measurements at 2, 4, 8, and 16 kHz were conducted prior to the acoustic injury and at 24 hours, 2 weeks, 4 weeks, 8 weeks, and 10 weeks post-injury. After the terminal 10-week ABR recording session, animals were euthanized and cochlear tissues were fixed, micro-dissected, and immuno-labeled with markers for visualization and quantification of HCs. Cochleae from siHES1 NP-treated, noise-exposed guinea pigs exhibited a marked restoration of both inner and outer HC numbers relative to cochleae from noise-exposed guinea pigs treated with non-targeting scRNA NPs (FIGS. 9-10).

Figure 11:
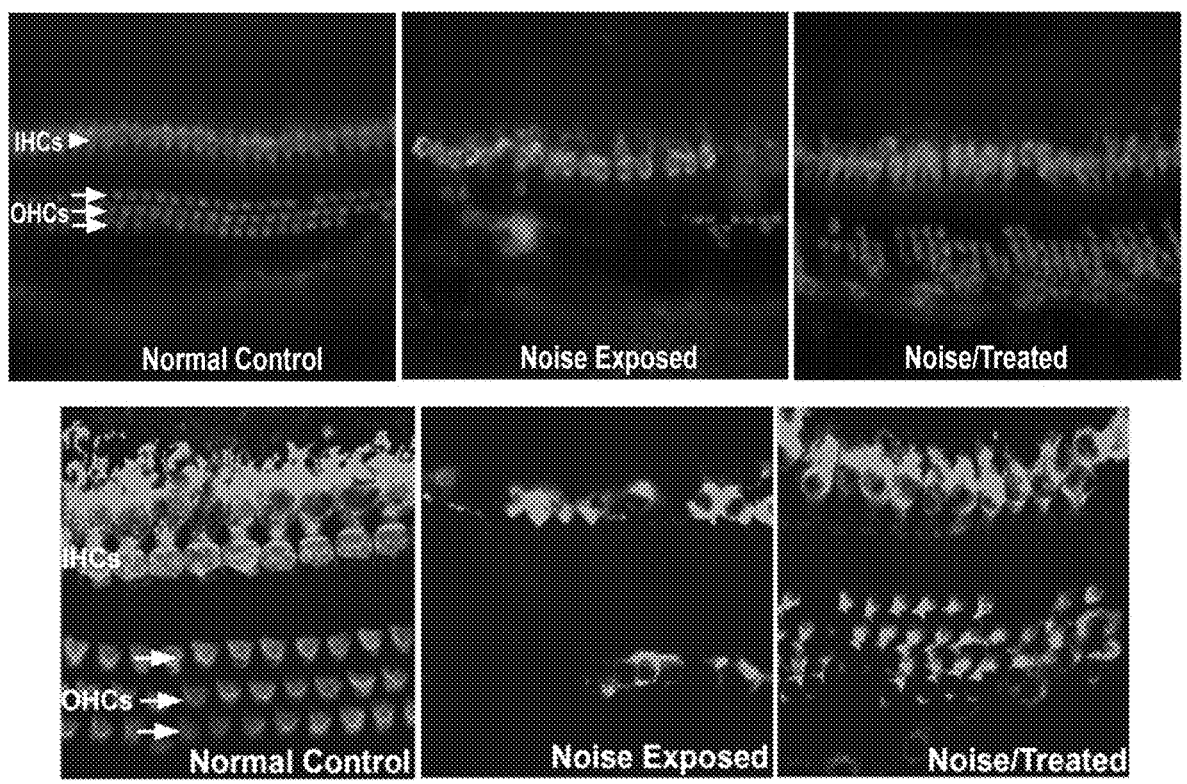
FIG. 11 depicts images collected from the basal turn of the cochlea, demonstrating that siHES1 NP infusion restores HC numbers in vivo in mature mice exposed to a loud damaging noise that kills hair cells. Four-week-old C57BL/6 mice were exposed to an acoustic overexposure of 8-16 kHz octave band noise at 116 dB SPL for 2 h. Seventy-two hours after the acoustic trauma, siHES1 NPs (800 µg/mL) were unilaterally-infused into the posterior semicircular canal, using a mini-osmotic pump, for seven days. Eight weeks after the noise injury, tissues were fixed and harvested for Myo7a-immunolabeling of HCs. siHes1 NP infusion resulted in increased HC numbers in architecturally-correct positions in noise-damaged mouse cochleae in vivo.

Mature C57BL/6 mice (4-wk-old) were exposed to an acoustic overexposure (8-16 kHz octave band noise, 116 dB SPL) for two hours. Seventy-two hours after the injury, mini-osmotic pumps loaded with 800 µg/mL of siHES1 NPs were surgically implanted into posterior semicircular canal, and the therapeutic treatment was unilaterally-infused over the course of seven days, after which the pumps were surgically removed. Eight-weeks post-treatment, animals were euthanized and cochlear tissues were fixed, micro-dissected, and immunolabeled with anti-Myo7a for visualization and quantification of HCs. Cochleae from siHES1 NP-treated, noise-exposed mice exhibited a marked restoration of both inner and outer HC numbers (in architecturally-correct positions) relative to cochleae from noise-exposed controls (FIG. 11).

In Vitro Drug Release Studies

In vitro drug release study from Hes1 siRNA-loaded PLGA NPs was performed in triplicate using a dialysis method adapted from Wangemann P, Schacht J, Dallos P, Popper A N, Fay R R (Eds.), The Cochlea, Springer, New York, 1996, pp. 130-185. Specifically, 1 mg of powdered PLGA NPs containing Hes1 siRNA or encapsulated (free) Hes1 siRNA were suspended in an inner dialysis bag (Spectra/Por Float-A-Lyzer G2, MWCO 20 kDa, Spectrum Laboratories Inc., Rancho Dominguez, Calif.) containing 1 mL of simulated perilymph media (SPM) without protein. The bag containing the colloidal suspension was placed in 3 ml of simulated endolymph media (SEM). The system was placed in a horizontal water bath (VWR Scientific Water Bath Model 1211, Sheldon Manufacturing Inc., Cornelius, Oreg.) at 37° C. Three 10 µL aliquots of SEM were withdrawn at specified time intervals and replaced with 304, of fresh SEM to maintain sink conditions. The average percent drug release (% ±Standard Deviation) was calculated at each time point interval (1-10 days).

|  | Loading efficiency of siRNA (pmo/mg NP) | Inoculum (pmol of siRNA) |
|---|---|---|
| Free siHES1 | — | 150 |
| siHES1-NPs#1 | 35 | 35 |
| siHES1-NPs#2 | 150 | 150 |

Release kinetics of siRNA from PGLA nanoparticles can be determined using the following equations known in the art:

Zero Order:

$$Q_t = Q_0 + K_0 t$$

(the drug release rate is independent of its concentration of the dissolved substance.)

First Order:

$$\text{Log } Q_t = \text{Log } Q_0 + Kt/2.303$$

(the drug release rate depends on its concentration)

Hixson-Crowell:

$$\sqrt[3]{Q_0} - \sqrt[3]{Q_t} = K_{HC} \times t$$

(the drug is released by dissolution)

Higuchi:

$$Q_t = K_H t^{1/2}$$

(the drug is released by diffusion)

Korsmeyer-Peppas:

$$F = (M_t/M) = K_m t^n$$

($n = 0.50$ indicates fickian diffusion $0.5 < n < 0.89$ indicates anomalous diffusion or non-Fickian diffusion: combination of both diffusion and erosion controlled rate release.

If $n \geq 0.89$ indicates case-2 relaxation or super case transport-2: erosion of the polymeric chain.)

|  | zero order | | First order | | Hixson-Crowell | | Higuchi | | Korsmeyer-Peppas | |
|---|---|---|---|---|---|---|---|---|---|---|
|  | $k_0$ | $R^2$ | K | $R^2$ | $K_{HC}$ | $R^2$ | $K_H$ | $R^2$ | n | $R^2$ |
| Free siRNA | 0.077 | 0.97 | −0.062 | 0.40 | 0.015 | 0.91 | 5.068 | 0.99 | 0.50 | 0.99 |
| Free HES1 siRNA is released by diffusion, not dependent on its dissolved concentration | | | | | | | | | | |
| NP1 | 0.103 | 0.92 | −0.005 | 0.97 | 0.006 | 0.95 | 3.436 | 0.89 | 0.94 | 0.96 |
| HES1 siRNA in NPs is released by dissolution and polymer erosion, release is concentration-dependent | | | | | | | | | | |
| NP2 | 0.089 | 0.94 | −0.007 | 0.99 | 0.008 | 0.99 | 3.903 | 0.91 | 0.97 | 0.94 |
| HES1 siRNA in NPs is released by dissolution and polymer erosion, release is concentration-dependent | | | | | | | | | | |

Figure 12:
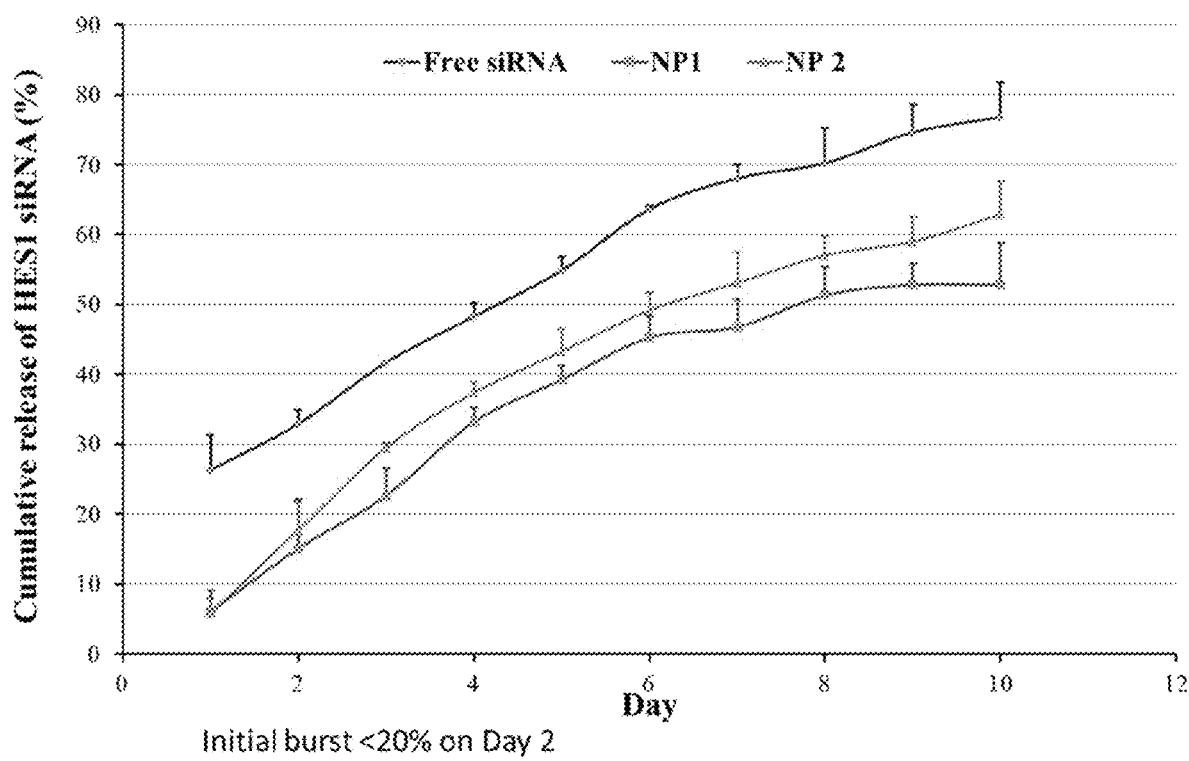
FIG. 12 is a graph of the cumulative release profile of HES1 siRNA from PLGA nanoparticles in perilymph-simulated media.

The release profile of the free Hes1 siRNA fit well with the zero order model ($R^2 = 0.97$) (FIG. 12). This indicated that the drug release rate was not dependent on the amount of the soluble siRNA in the external simulated endolymph medium (SEM). Therefore, irrespective of the concentration of the soluble siRNA in simulated perilymph medium (SPM), the free Hes1 siRNA diffused constantly through the semi-permeable membrane (percent release rate 6.6%/day). The significant initial migration of Hes1 siRNA (20%, 1 day) across the semi-permeable membrane into the external SEM at the earliest sampling interval is consistent with passive diffusion of a free solute.

In contrast to the free Hes1 siRNA, the release profile of Hes1 siRNA encapsulated within PLGA NPs revealed a sustained release profile fit with first order ($R^2 = 0.97$), Hixson-Crowell ($R^2 = 0.95$) and Korsmeyer-Peppas ($R^2 = 0.96$, $n = 0.94$) equations (See Figure). This diffusion pattern indicated that the release was mainly governed by dissolution of Hes1 siRNA through the delayed hydrolytic degradation of the polymeric shell (PLGA) of the NPs. Moreover, the dissolution of Hes1 siRNA was accompanied with the erosion of the polymeric chain of PLGA.

Pairwise comparison of the release profile of siRNA from NP suspension 1 (NP1) and NP suspension 2 (NP2) indicated that the release rate was increased with increased siRNA loading in the NP (percent release rate: 5.9 vs 6.3%/day, respectively). This indicated that the drug release rate was dependent on the amount of the soluble siRNA in the external SEM. The low initial burst release of Hes1 siRNA (~5%, 1 day) for both NP formulations is interpreted to be due to the presence of siRNA adsorbed on the surface of the NPs.

For free siRNA, it required 4.2 days to release 50% of the initial loading in this drug release model system. For NP1 it required 7.8 days to release 50% of the initial loading. For NP2 it required 6.2 days to release 50% of the initial loading.

Example 2-BIO and Hes1 siRNA

Undamaged OCs

Figure 13:
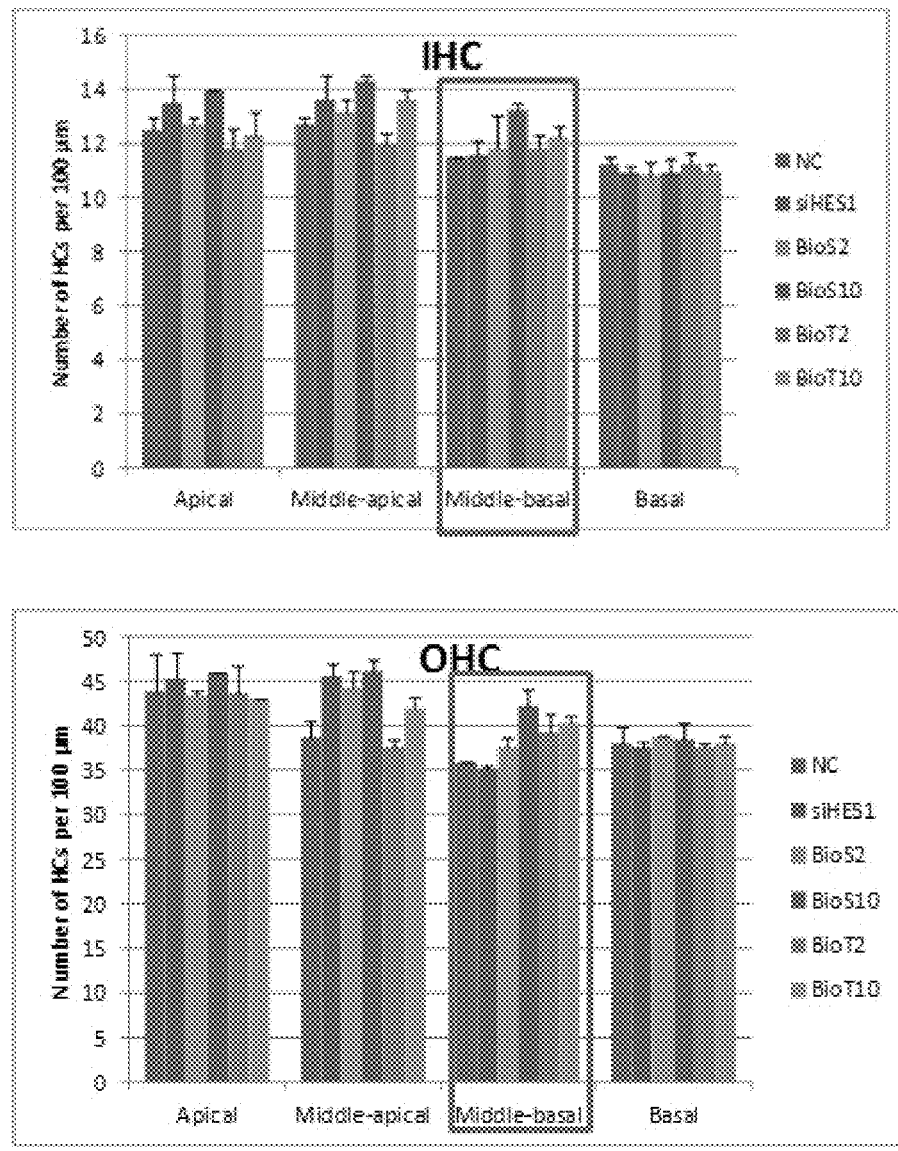
FIG. 13 depicts the effects of siHES1 either alone or in combination with staged (S) or simultaneous (together, 7) application of the GSK-3 inhibitor, BIO, on increasing inner and outer HC (IHC and OHC, respectively) numbers in undamaged postnatal (P3) organotypic cultures of Corti's organ. Organs of Corti (OCs) were cultured in media alone for 24 hours prior to the addition of media containing either vehicle alone (dimethyl sulfoxide, DMSO) or the GSK-3 inhibitor, BIO, at concentrations of 2 or 10 micromolar (for staged application, 5). After an additional 72 hours in culture, the media was exchanged and replaced with culture medium containing either DMSO (for normal controls, NC, or staged, S, application experiment) or BIO at 2 or 10 micromolar (for simultaneous application, 7) in the presence or absence of 20 nM of siHES1 transfection complexes (JeSI 10 mM, Polyplus Transfection, Illkirch, France). After an additional 48 hours, all media was replaced with basal medium and cultured for an additional 48 hours prior to fixation and immunolabeling of HCs with anit-Myo7A. Sequential application of 10 micromolar BIO followed by transfection with siHES1 resulted in the greatest increase in both IHC and OHC numbers (i.e. more de novo hair cell production) in undamaged OCs, with the greatest distinctions observed in the mid-basal turn of the OC, a region that is typically recalcitrant to new HC production in postnatal cochleae.
Figure 14:
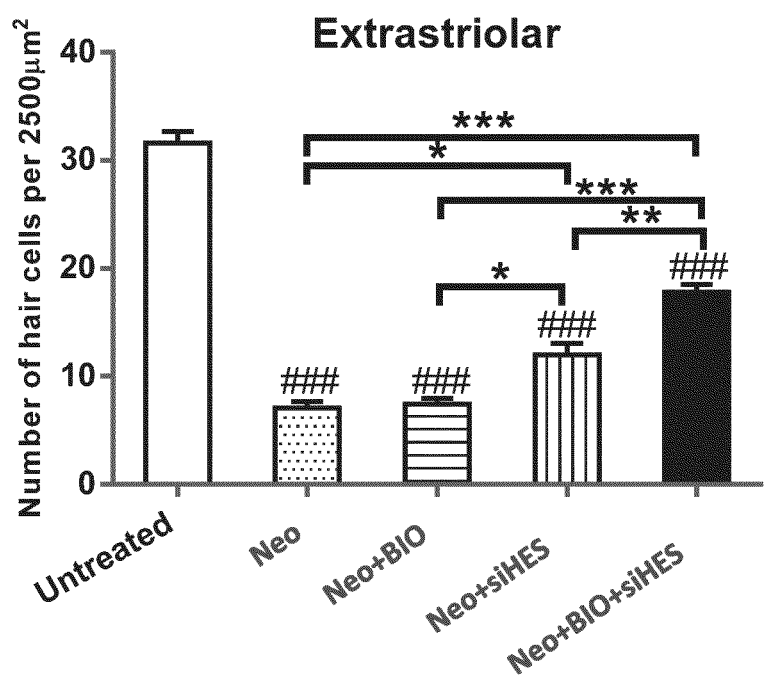
FIG. 14 shows the results of combinatorial treatment with BIO and siHes1, demonstrating a synergistic increase in the number of HCs in the extrastriolar region of ototoxin-ablated utricles relative to treatment with either single therapeutic agent alone. To assess whether BIO can enhance the therapeutic efficacy of Hes1 siRNA in regenerating HCs following a toxic insult, neonatal murine utricular tissues were exposed to neomycin (NEO) and then either left untreated or were treated with one or both of the therapeutic agents. After a total of 8 days in vitro, tissues were fixed and labeled with the HC marker, Myo7a. ###, $p<0.001$ difference in Myo7a-postive cells relative to untreated controls. *, , and *, $p<0.05$, 0.01, and 0.001, respectively, with respect to significant differences in the number of Myo7a-postive cells between treatment groups.
Figure 15:
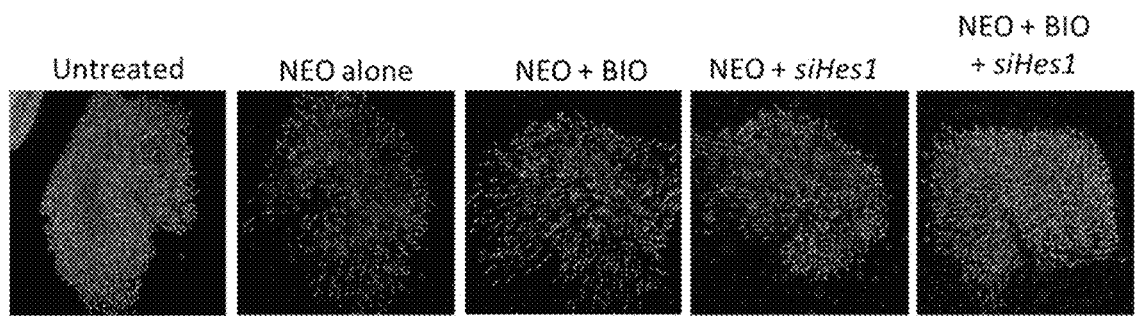
FIG. 15 depicts representative images from the different experimental groups from FIG. 14. Following NEO treatment, HC numbers are greatly reduced (panel 2). Hes1 siRNA treatment alone resulted in increased HC numbers, primarily within the striolar region (panel 4), while combinatorial treatment with siHES1 and BIO resulted in an enhanced regenerative response that also spanned the extrastriolar region (panel 5).
Figure 16:
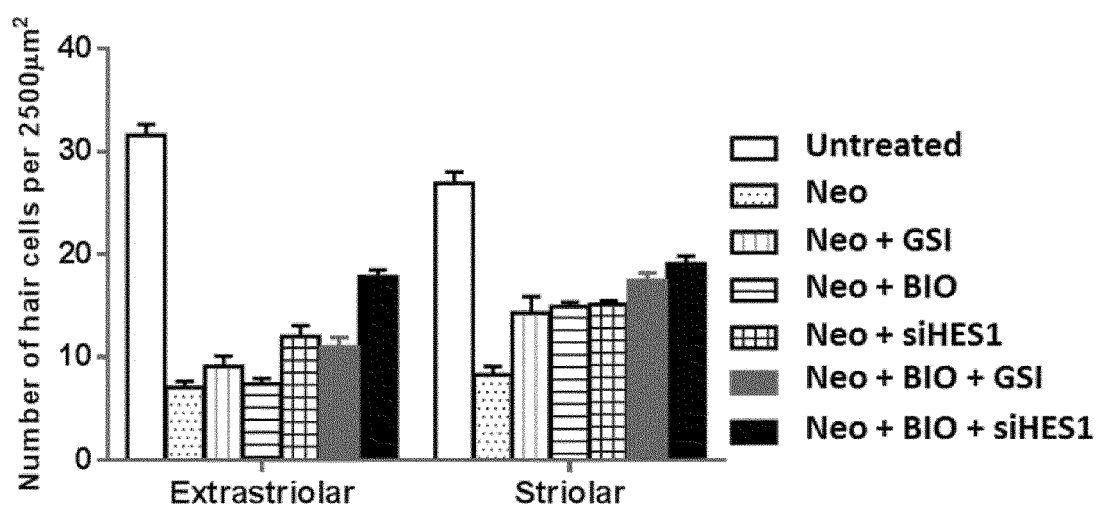
FIG. 16 demonstrates that staged treatment with BIO and siHes1 resulted in a more robust transdifferentiative response in the extrastriolar region of NEO-ablated utricles than that observed for either BIO or siHES1 alone or for staged treatment with BIO plus a gamma-secretase inhibitor (GSI), deshydroxy LY 411575 (dibenzazepine, 5 µM), where the combinatorial treatment effect was largely restricted to the striolar region of the utricular explant.
Figure 17:
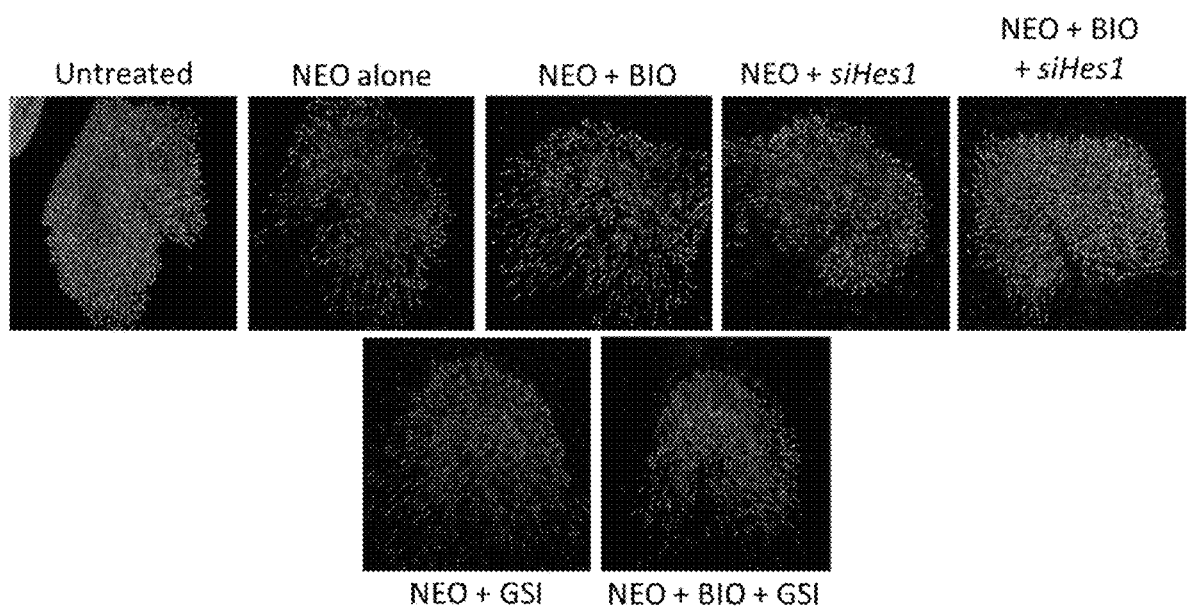
FIG. 17 depicts representative images from the different experimental groups from FIG. 16. Following NEO treatment, HC numbers are greatly reduced (panel 2). Individually, BIO, Hes1 siRNA and GSI treatment alone resulted in increased HC numbers within the striolar region (panels 4 and 6), while combinatorial treatment with BIO and siHES1 uniquely resulted in an enhanced regenerative response that also spanned the extrastriolar region (panel 5).
Figure 18:
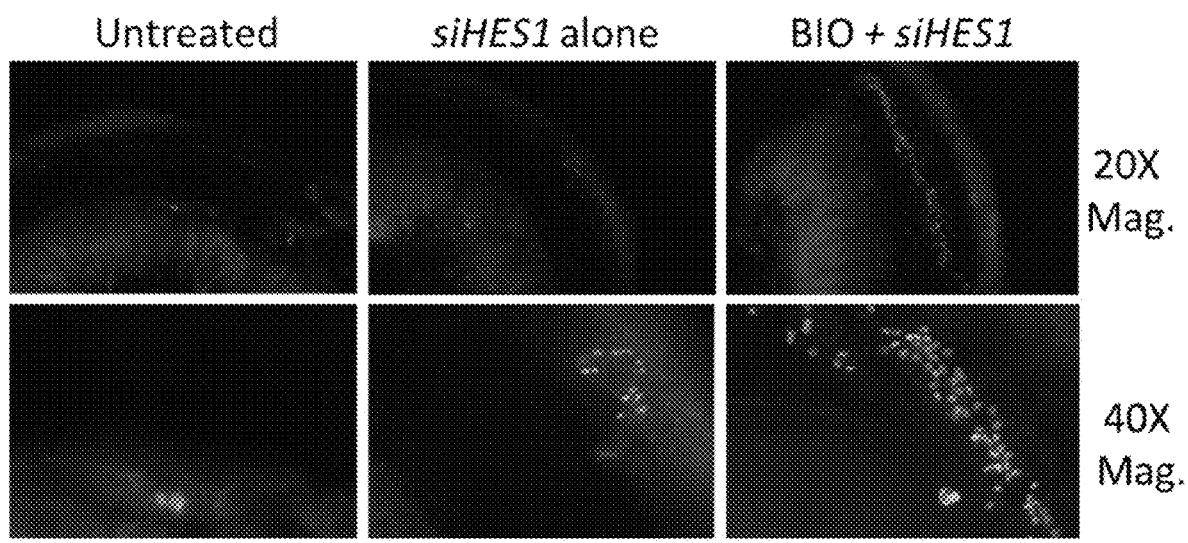
FIG. 18 depicts representative images from a whole cochlear culturing model of mature murine OCs, showing the middle turn of the different experimental groups shown here at 20× and 40× magnifications. Using this whole cochlear culturing model to study HC regeneration, mature murine cochleae (P16) were harvested and incubated for 24 h in media alone, a period over which pre-existing IHCs and OHCs rapidly degenerate and die. After 24 h in culture, these cultures were treated with 5 µM BIO for 72 h followed by transfection with siHES1 (20 nM) and subsequent culturing for a total of 9 days in vitro, at which time tissues were fixed and labeled with phalloidin (red) or with the HC marker, Myo7a (green). Combinatorial treatment with BIO and Hes1 siRNA resulted in a marked increase in HC numbers within the sensory epithelial region under these conditions (right panels).

Organotypic cultures from murine cochleae were cultured and then harvested on postnatal day 3 (P3) from CD1 mice. These explants were then cultured in appropriate media for twenty-four hours. On the equivalent of P4 (i.e. 24 h ex vivo), cultured organs of Corti (OCs, i.e. cochlear sensory epithelia) were bathed in fresh culture media containing either DMSO (vehicle) or the GSK3 inhibitor, 6-bromoindirubin-3'-oxime (BIO), and the OCs were cultured accordingly for 72 h. On the equivalent of P7 (i.e. 96 h ex vivo), a subset of cultures from both treatment groups are transfected (jetSI 10 mM, PolyPlus Transfection, Illkirch, France) with 20 nM Hes1 siRNA for 24 h. For examining the effects of sequential application, siHes1 was transfected in media without BIO. For examining the effects of simultaneous application, siHes1 was transfected in media containing BIO. Following the 24 h transfection incubation period, cultures designated for the examination of sequential treatment of the two agents were cultured in media without BIO, whereas cultures designated for simultaneous application were cultured in the presence of BIO for an additional 48 h. All cultures were maintained in media without either of the test agents for a final 24 h, after which tissues were fixed in 4% paraformaldehyde solution and subjected to immunolabeling with an antibody against the hair cell marker, myosin VIIa (Myo7a), and an appropriate secondary antibody for subsequent immunofluorescence-mediated quantification of HCs along the length of the cochlear spiral (FIG. 13).

NEO Damaged Utricles

Organotypic cultures from murine utricular maculae (balance organ sensory epithelia) were cultured and then harvested on postnatal day 3 (P3) from CD1 mice. These explants were then cultured in appropriate media for twenty-four hours. On the equivalent of P4 (i.e. 24 h ex vivo), cultured utricles were bathed in fresh culture media containing the ototoxic aminoglycoside neomycin (NEO) for 24 h to induce HC loss and then administered the either DMSO (vehicle) or the GSK3 inhibitor, 6-bromoindirubin-3'-oxime (BIO, 2.5 µM) on P5. The utricles were cultured accordingly for 72 h. On the equivalent of P8 (i.e. 120 h ex vivo), cultures were replaced with fresh media without therapeutics and a subset of cultures from both treatment groups were transfected (jetSI 10 mM, PolyPlus Transfection, Illkirch, France) with 20 nM Hes1 siRNA or incubated in the presence of 5 µM of the Notch Pathway inhibitor, LY411575, and cultured for an additional 72 h. All cultures were then maintained in media without either of the test agents for a final 24 h, after which tissues were fixed in 4% paraformaldehyde solution and subjected to immunolabeling with an antibody against the hair cell marker, myosin VIIa (Myo7a), and an appropriate secondary antibody for subsequent immunofluorescence-mediated quantification of HCs along the length of the cochlear spiral (FIGS. 14-17).

In all cases, BIO/siHes1 generates greater numbers of de novo HCs than either agent alone and sequential treatment will induce a more robust response than simultaneous treatment. These results are consistent with sequential application resulting in a greater transdifferentiative response (i.e. more de novo hair cells), particularly in the mid-basal turn of the OC and extrastriolar regions of the utricule, regions that are typically recalcitrant to new HC production in postnatal cochleae and utricular maculae (FIGS. 13-18).

Example 3-TIDE and Hes1 siRNA

Analysis of Tideglusib

Tideglusib was procured from Cayman Chemical Company and performed a dose curve analysis under serum starvation conditions with Madin-Darby Canine Kidney (MDCK) cells in parallel with a series of commercially-available GSK3 inhibitors to ascertain its relative proliferative potential under mitotically-suppressed conditions in this well-established mammalian epithelial cell line. In these experiments, MDCK cells were cultured under serum starvation conditions for 24 hours prior to culturing cells for 48 hours in the presence of GSK3 inhibitors and 10 µM EdU (5-ethynyl-2'-deoxyuridine), a nucleoside analog that permanently marks cells that have undergone DNA replication.

Figure 19:
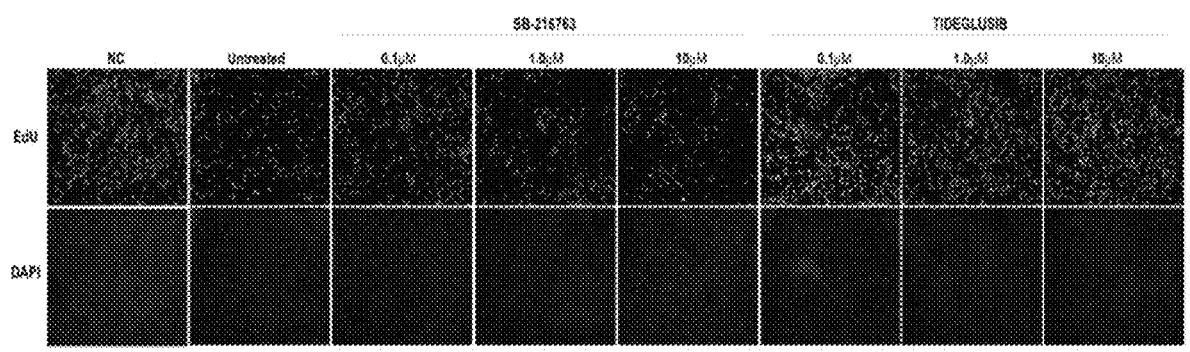
FIG. 19 depicts representative images of GSK3I-mediated proliferation in serum-starved MDCK cells. Cells were initially cultured in the presence of 10% fetal bovine serum (FBS) and then switched to serum-free media for 24 hours prior to the addition of 0.2% serum-containing media which included GSK3Is at the indicated concentrations in the presence of 10 µM EdU. Cells were cultured an additional 48 h prior to fixation and visualization of EdU-positive nuclei (green) via conjugation of AlexaFluor488 azide in a copper-catalyzed cycloaddition ("Click" reaction, Click-iT Edu, Life Technologies). Total nuclei were stained with DAPI (blue). NC, normal control or untreated cells cultured in the presence of 10% FBS throughout the experimental time course. The GSK3I, Tideglusib supported a sustained proliferative response across the dose range tested, while the proliferative response induced by other GSK3Is, such as SB-216763, became progressively attenuated with escalating doses.

An example of this type of analysis is depicted in FIG. 19. Each of the GSK3 inhibitors that were tested exhibited an apparent positive effect on cell proliferation at the lowest doses tested under these conditions, dose escalation (up to 10 µM) resulted in reductions in the number of EdU-positive nuclei observed. Tideglusib sustained its positive effect on cell proliferation at higher doses under these conditions, perhaps underscoring the greater specificity (i.e. noncompetitive inhibitor of ATP) of this pharmacologic inhibitor for GSK3.

Figure 20:
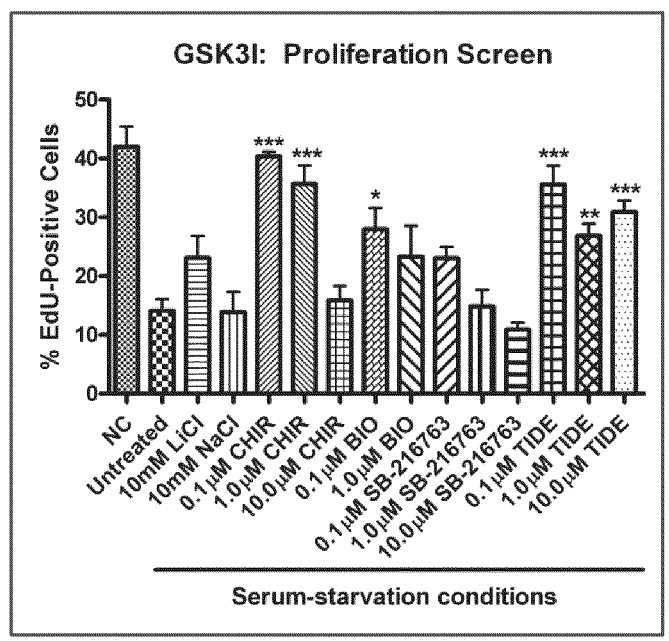
FIG. 20 shows results of a comparison of GSK3 inhibitors for inducing a proliferative response in serum-starved (i.e. mitotically suppressed) MDCK cells. EdU-positive nuclei from imaged fields of MDCK cells cultured as described in FIG. 13 were quantified using ImageJ software (NIH) and graphed as the averaged percentile of the number of EdU-positive cells relative to the total number of DAPI-stained nuclei in each field. A minimum of four fields of cells for each experimental condition were included in this analysis. (* and ***, p<0.05 and 0.001, respectively, for statistically significant increases in EdU-positive nuclei relative to untreated, serum-starved controls). Among the GSK3Is examined in this targeted analysis, Tideglusib supported the most robust mitotic response at the GSK3I concentration ranges tested under these serum-limiting conditions.

Formal quantification of EdU-positive nuclei in each of the treatment groups from this screen is depicted in FIG. 20. Incubation with 10 mM LiCl, a molecule with well-documented GSK3 inhibition at high doses, resulted in increased numbers of EdU-positive cells, relative to an identical dose of sodium chloride, a non-inhibitory salt. Among the pharmacologic GSK3Is evaluated in this analysis, low-dose (0.1 µM) CHIR-99021 (CAS 252917-06-9) resulted in robust, statistically-significant increase in mitotically-active cells cultured under serum starvation. Dose-escalation to 10 µM dramatically reduced the positive effects on proliferation observed at low doses, such that the number of EdU-positive nuclei became statistically insignificant relative to untreated, serum-starved cells. Similar dose-dependent trends of reduced proliferative efficacy were also observed for the other ATP-competitive GSK3Is, such that escalating doses of 6-Bromoindirubin-3'-oxime (BIO, CAS 667463-62-9) and SB-216763 (CAS 280744-09-4) resulted in reduced numbers of EdU-positive nuclie, with high-dose (10 µM) BIO proving to be toxic (i.e. not quantified) to MDCK cells under these conditions. The number of EdU-positive nuclei remained statistically higher than those quantified in untreated, serum-starved MDCK cell populations over each of the doses that were tested. These results suggest that the greater predicted specificity for GSK3 may translate into a broader concentration range for proliferation.

Figure 21:
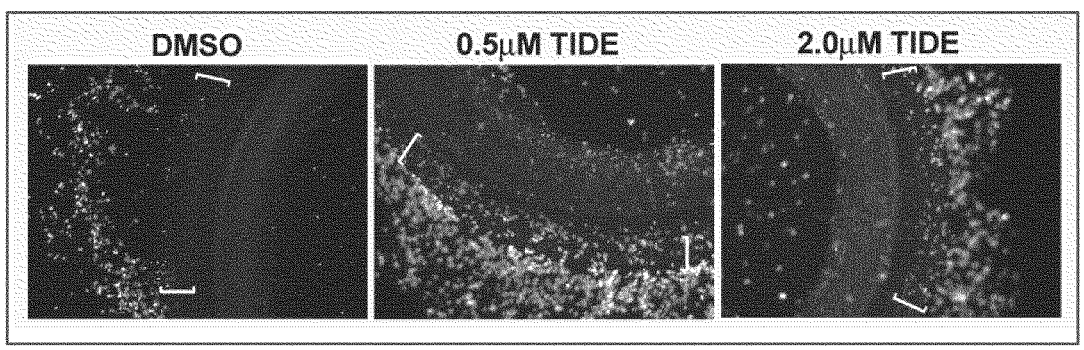
FIG. 21 depicts EdU-labeling of mitotically-active cells in the postnatal organ of Corti in response to Tideglusib treatment. Postnatal day 3 OCs were harvested and cultured in vitro for 24 hours prior to the addition of culture media containing 10 µM EdU in the presence of either vehicle alone (DMSO) or tideglusib (TIDE) at a final concentration of 0.5 or 2.0 µM. Organotypic cultures were cultured continuously in the presence of these agents for 72 hours prior to fixation and visualization of EdU-positive nuclei as described above. Images of the middle turn of the OC from each group are shown. Brackets denote the sensory epithelial region in each image. In comparison to vehicle-treated controls, tideglusib induced a markedly greater mitotic response in the sensory epithelial region of the cultured organs of Corti.

A targeted pilot experiment was conducted in which postnatal OCs were cultured continuously for 72 hours in the presence of EdU and either tideglusib or vehicle alone to assess whether the GSK3 inhibitor was capable of inducing a mitotic response in the sensory epithelial region of the OC. As shown in FIG. 21, OCs cultured in the presence of tideglusib at concentrations of 0.5 and 2.0 micromolar exhibited a greater incidence of EdU-positive nuclei in the anatomical position of the auditory sensory epithelium than that observed in OCs cultured in the presence of vehicle alone. Follow-up analyses will indicate whether this tideglusib-induced proliferative response in the OC involves supporting cells, hair cells, or both, using cell type-specific markers.

Undamaged and NEO Damaged OCs

Figure 22:
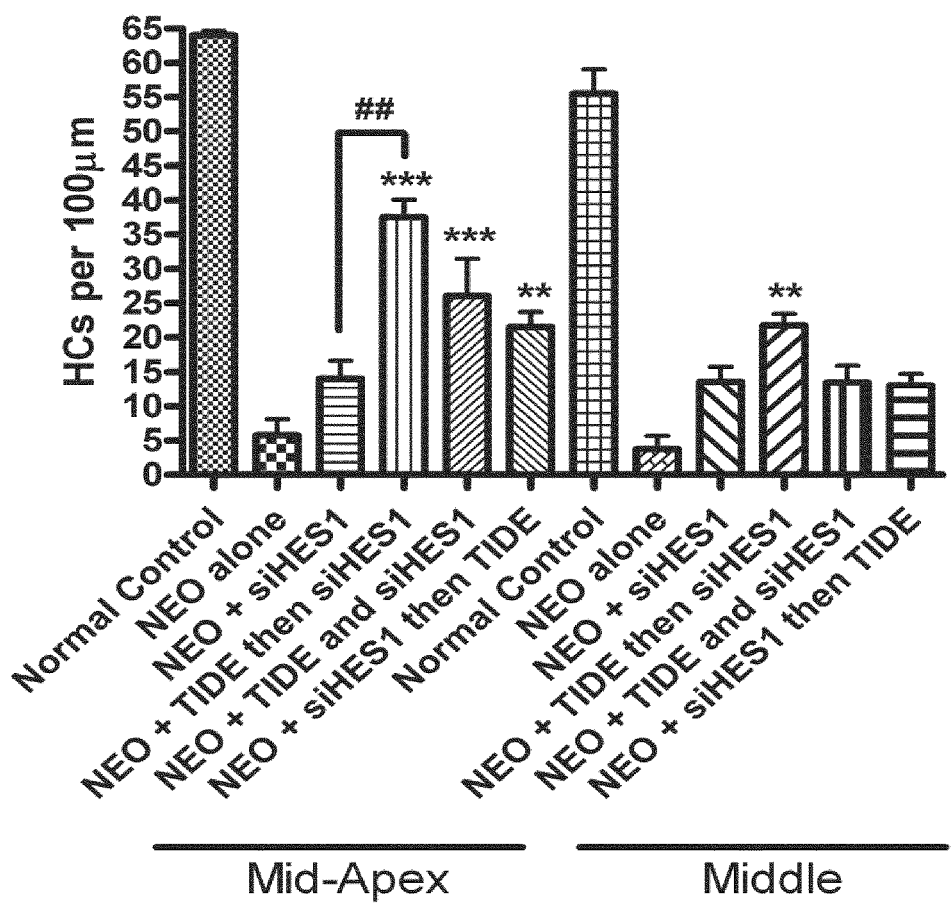
FIG. 22 depicts hair cells (Myo7a+ cells) quantified from the mid-apical and middle regions of organotypic cultures of murine OCs following a 24 h exposure to neomycin (0.7 mM) and subsequent recovery in the presence or absence of the GSK3 inhibitor Tideglusib (TIDE) and/or siHES1 (20 nM) lipofection complexes (JetSI, Polyplus). Greater HC numbers were observed in both the mid-apical and middle turns of the OC in cultures treated with a combination of TIDE and siHES1, with a staged application of TIDE then siHES1, giving rise to the most significant increase in HC numbers.  and *, p<0.01 and 0.001 in comparison to NEO treatment alone. ##, p<0.01 in comparison to NEO+siHES1 treatment.
Figure 23:
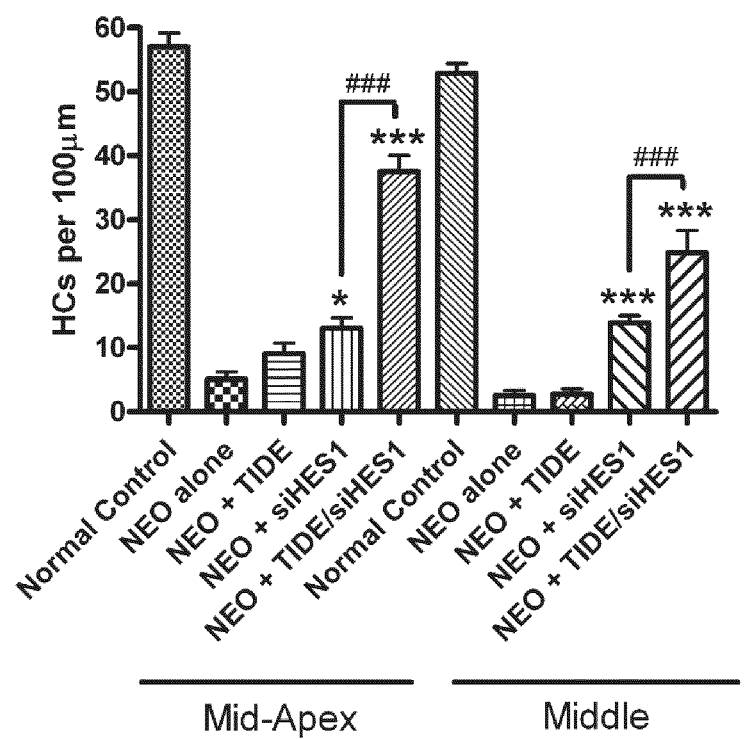
FIG. 23 depicts hair cells (Myo7a+ cells) quantified from the mid-apical and middle regions of organotypic cultures of murine OCs following a 24 h exposure to neomycin (0.7 mM) and subsequent recovery in the presence or absence of the GSK3 inhibitor Tideglusib (TIDE) and/or siHES1 (20 nM) lipofection complexes (JetSI, Polyplus). Although greater HC numbers were observed in both the mid-apical and middle turns of the OC in cultures treated with siHES1 at 72 h post-neomycin, a staged combination of TIDE then siHES1 treatment gave rise to a synergistic increase in HC numbers in both the middle and mid-apical turns of the OC. * and ***, p<0.05 and 0.001 in comparison to NEO treatment alone. ###, p<0.01 in comparison to NEO+siHES1 treatment.
Figure 24:
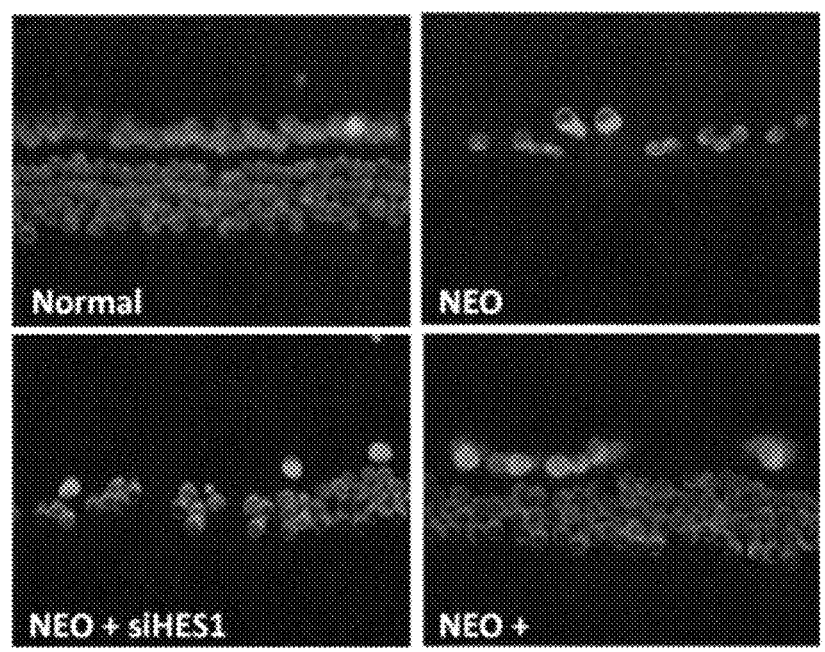
FIG. 24 depicts Myo7a immunolabeling of the of the middle turn of the OC from controls and treatment groups among NEO-damaged organotypic cultures from the experiment described in FIG. 23.

The protocol described above for BIO is used, substituting the addition of BIO for 10.0 µM Tideglusib (TIDE). A third treatment group is added, where Tideglusib is included in the culture medium after siHes1, parallel to the other protocols: on P4 or P5 (depending on whether there was an ototoxic insult to simulate hair cell loss) the control media is added with or without the inclusion of 10.0 µM TIDE; on P7 siHes1 is added in the presence of absence of TIDE; and on P9 10.0 µM Tideglusib is included in the media for a subset of cultures. On P11, all media is replaced with fresh media without any therapeutics. On P12, the tissues are fixed for immunolabeling. An example of comparative analyses from this treatment paradigm, following an exposure to the ototoxic aminoglycoside, NEO, is depicted in FIG. 22. Greater HC numbers were observed in the mid-apical turns of ototoxin-exposed OCs in cultures treated with a combination of TIDE and siHES1, with a staged combination of TIDE and siHES1 giving rise to the most significant increase in HC numbers under these conditions (FIGS. 22-24). HC quantification results for the data in FIG. 22 are shown in the table below.

| Experimental Group | Hair Cell Counts ± SEM | |
| --- | --- | --- |
|  | Mid-apical turn | Middle Turn |
| Normal Control | 57.0 ± 2.2 | 52.9 ± 1.6 |
| NEO alone | 5.1 ± 1.1 | 2.5 ± 0.8 |
| NEO + TIDE | 9.1 ± 1.6 | 2.8 ± 0.8 |
| NEO + siHES1 | 13.0 ± 1.7 | 13.9 ± 1.1 |
| NEO + TIDE then siHES1 | 37.5 ± 2.5 | 24.9 ± 3.4 |
| NEO + TIDE and siHES1 | 26.0 ± 5.4 | 13.4 ± 2.5 |
| NEO + siHES1 then TIDE | 21.6 ± 2.2 | 13.0 ± 1.7 |

The experiment was repeated using the staged application of TIDE and siHES1 described above, the results from which underscore the significant enhancement of siHES1 efficacy for restoring HC numbers following pre-application of TIDE in a manner that indicates synergism between the agents (FIG. 23-24).

Figure 25:
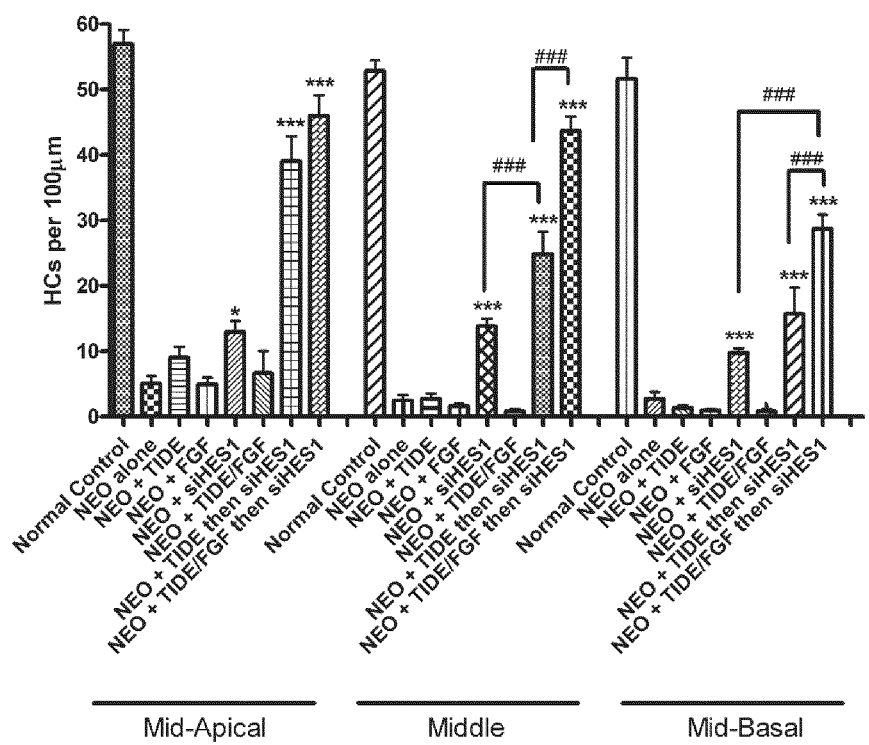
FIG. 25 depicts hair cells (Myo7a+ cells) quantified from the mid-apical, middle, and mid-basal regions of organotypic cultures of murine OCs following a 24 h exposure to neomycin (0.7 mM) and subsequent recovery in the presence or absence of the GSK3 inhibitor Tideglusib (TIDE) and/or siHES1 (20 nM) lipofection complexes (JetSI, Polyplus). One set of NEO-ablated OCs were treated with TIDE then siHes1 in the presence of 2 ng/mL FGF-2 as a media supplement with the aim of potentially enhancing the effects of Tideglusib. Greater HC numbers were observed in both the mid-apical and middle turns of the OC in cultures treated with a staged combination of TIDE and siHES1, while the addition of FGF-2 to the growth media potentiated the effects through the mid-basal turn of the OC, an area that is typically more recalcitrant to HC regeneration. * and ***, p<0.05 and 0.001 in comparison to NEO treatment alone. ###p<0.01 in comparison to NEO+siHES1 treatment or among treatment groups as noted.
Figure 26:
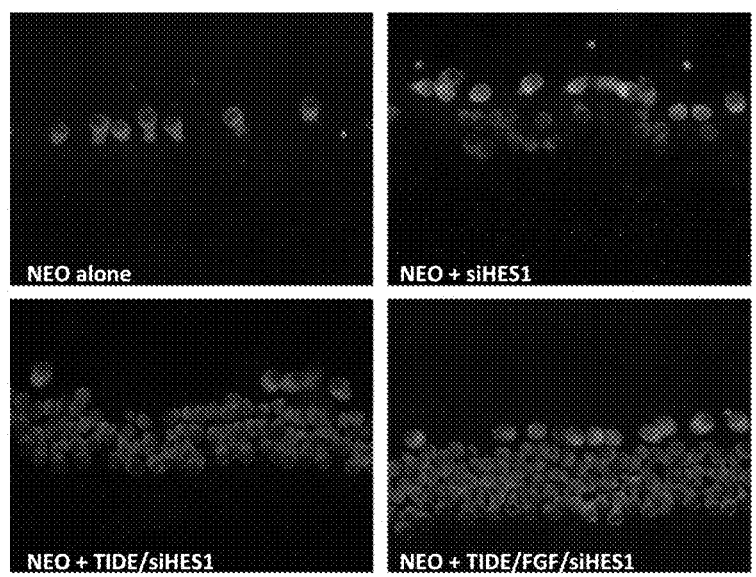
FIG. 26 depicts Myo7a immunolabeling of the middle turn of the OC from controls and treatment groups among NEO-damaged organotypic cultures from the experiment described in FIG. 25.
Figure 27:
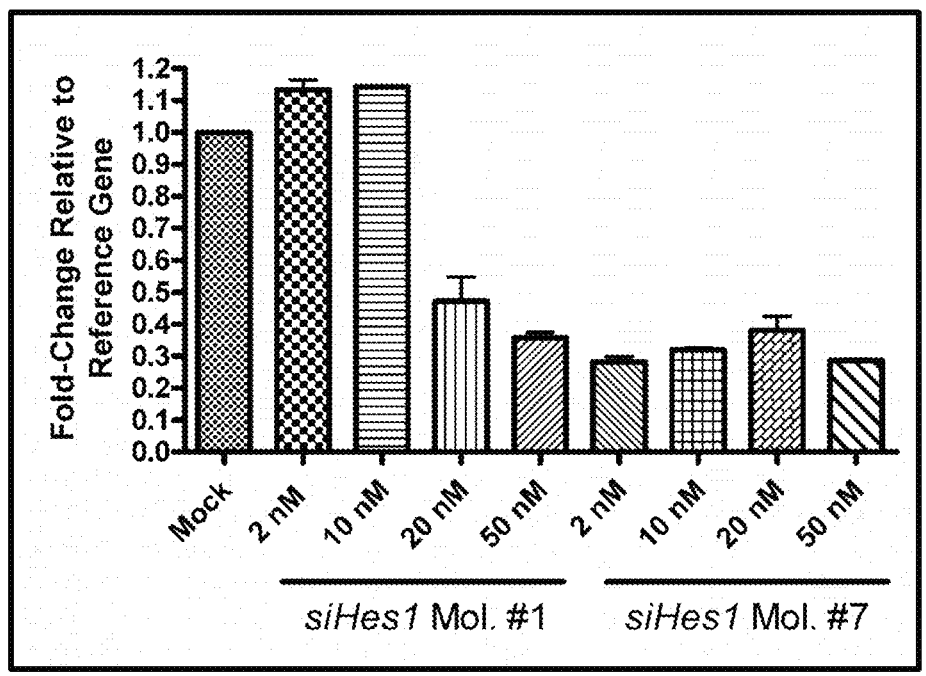
FIG. 27 depicts reverse transcription-quantitative polymerase chain reaction (RT-qPCR) results from comparative dose curve analyses of Hes1 knockdown efficiency relative to mock-treated controls in a murine inner ear cell line (IMO-2B1), using two distinct siHES1 molecules with conserved target sites among mammalian Hes1 transcripts. SiRNA molecules were transfected into sub-confluent wells of IMO-2B1, using a commercial transfection agent (RNAiMAX, ThermoFisher Sci.). Forty-eight hours after transfection, total RNA was isolated and subjected to RT-qPCR analyses, using primers against Hes1 and the house keeping gene GAPDH. Relative Hes1 levels were determined by the $2^{-\Delta\Delta CT}$ method (See Livak and Schmittgen (2001) Methods 25(4):402-408, incorporated by reference in its entirety). The apparent potency of molecule #7 for depleting Hes1 transcript levels was considerably greater than that of molecule #1, as optimal knockdown using molecule #7 was observed using as little as 2 nM siRNA (relative to ~20 nM required for molecule #1).
Figure 28:
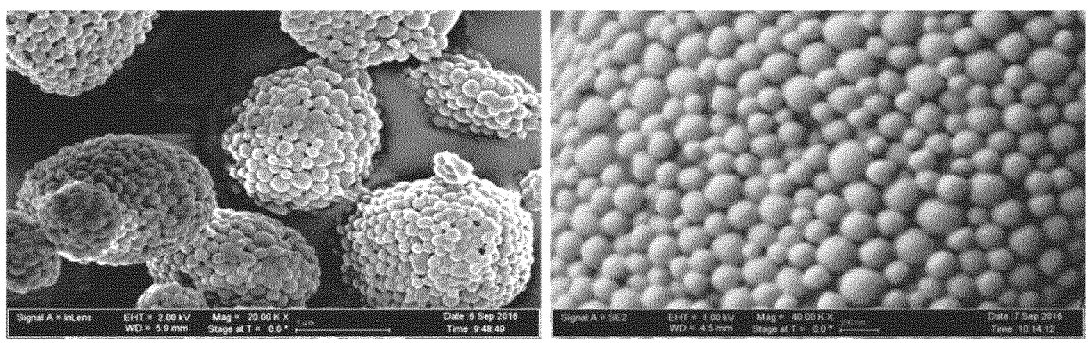
FIG. 28 depicts representative scanning electron microscopy (SEM) images of siHes1 PEG-PLGA NPs at 20,000 (left panel) and 40,000 (right panel)×magnification.

This experimental paradigm was again repeated adding additional treatment groups where FGF-2 was optionally included in the culture medium at 2 ng/mL at P5, P7, and P9 for a subset of cultures. Greater HC numbers were observed in both the mid-apical and middle turns of the OC in cultures treated with a staged combination of TIDE and siHES1, while the addition of FGF-2 (which did not elicit a therapeutic response on its own at this concentration) to the growth media potentiated the therapeutic effects of TIDE/siHES1 treatment through the mid-basal turn of the OC, an area that is typically more recalcitrant to HC regeneration in the postnatal mammalian cochlea (FIGS. 25-26).

Example 4-Further Nanoparticle Experiments

A subset of Experiments 2 and/or 3 are repeated using siHes1 loaded nanoparticles—sustained release formulations—and TIDE at various doses, as well as using nanoparticles comprising both siHes1 and TIDE.

In some replications of the protocol, co-application of a sustained release siHes1 nanoparticle and TIDE is conducted in a manner designed to mimic staged application of TIDE and siHes1 lipofection complexes. Mimicry is achieved using the neomycin protocol described in Experiments 2 and 3 adding TIDE (in some replications at escalating doses between 0.5 and 20 µm) and sustained release siHes1 nanoparticles applied simultaneously.

Further, all the above referenced experiments are repeated with siHes5 and siMAPK1.

An Exemplary Protocol Follows

Applicants hypothesized that the delayed, yet sustained, release of siHes1 from biocompatible PLGA NPs would recapitulate the therapeutic attributes of staged application of a GSK3 inhibitor and siRNA against Hes1 when the two drugs were co-administered. To test this hypothesis, a sub-maximal efficacious dose (60 nM) of siHes1 NPs with escalating doses (0.5, 2, and 10 µM) of the GSK3I, tideglusib, in order to have sufficient experimental margin were used to assess a regenerative dose-response profile in organotypic cultures of neomycin (NEO)—exposed organs of Corti (OCs). Using this paradigm, NEO-ablated OCs were subsequently cultured with siHes1 NPs alone or in combination with Tideglusib over the course of six days prior to fixation and immunohistological analyses.

Figure 37:
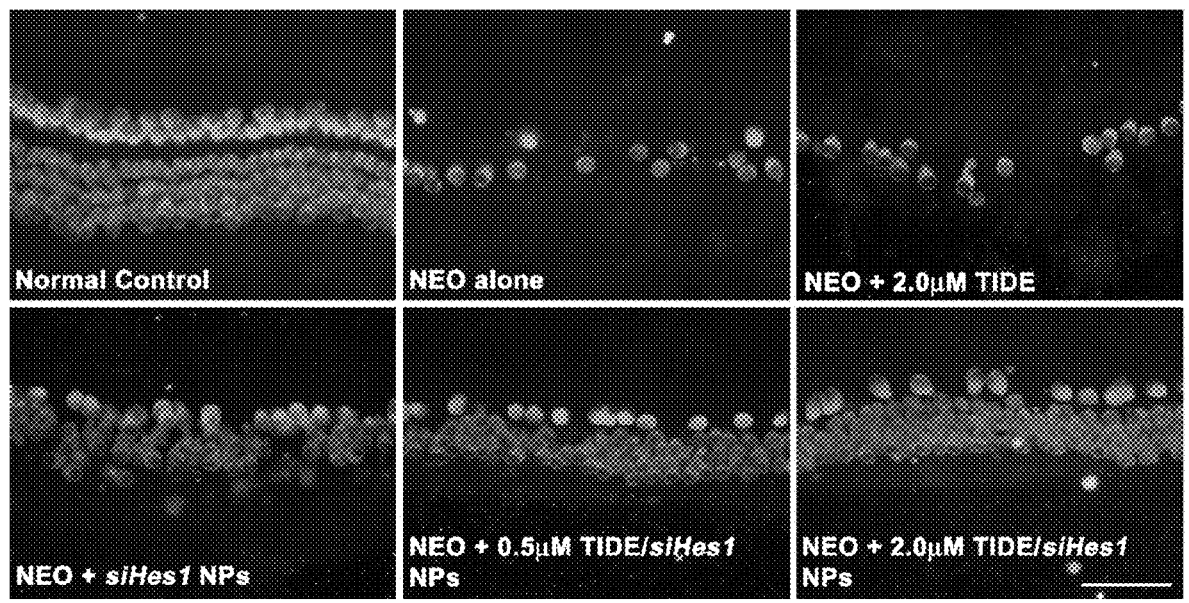
FIG. 37 shows that GSK3 inhibition synergizes with siHes1 NPs to restore HC numbers in ototoxin-ablated OCs. Postnatal (P3) murine (CD1) OC explants were exposed to the ototoxic aminoglycoside, neomycin, for 24 h and then treated with 60 nM siHes1 NP alone; the GSK3 inhibitor, Tideglusib (TIDE), alone (2 µM); or a combination of 60 nM siHes1 NP with escalating doses of Tideglusib (0.5, 2, or 10 µM) for 6d prior to fixation and immunolabeling against the HC-specific marker, Myo7a. Middle turn as fixed reference among images shown.
Figure 38:
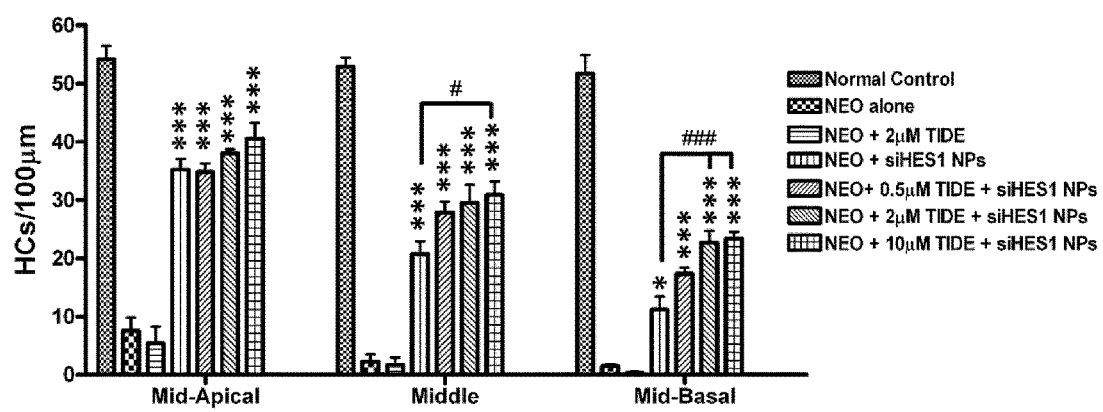
FIG. 38 shows that TIDE synergizes with siHes1 NPs to restore HC numbers in ototoxin-ablated OCs. NEO-ablated OCs were treated with a suboptimal (60 nM) dose of siHes1 NPs either alone or in combination with escalating doses of TIDE. HC quantification revealed a synergistic increase in HC numbers in the middle and mid-basal turns of the OC when Tideglusib and low-dose siHes1 NP treatments were combined. The sustained release profile of siHes1 NPs mimics staged application of the two therapeutics. Dose-dependent increases in hair cell densities were observed throughout the OC upon co-treatment with TIDE and siHes1 NPs. * and ***, p<0.05 and 0.001 in comparison to NEO treatment alone. # and ###, p<0.05 and 0.001 in comparison to NEO+siHes1 NP treatment. n=5 OCs/condition.

As shown in FIGS. 37 and 38, clear, concentration-dependent enhancement of siHes1 NP-induced hair cell (HC) regeneration was observed when OCs were treated in combination with escalating doses of Tideglusib. However, treatment with Tideglusib alone did not induce a statistically significant regenerative response, suggesting that it likely acts as a priming agent in this context to intrinsically enhance a siHes1-mediated response rather than acting independently to regenerate HCs.

Quantification of HCs numbers among these treatment groups revealed that the clinically-relevant GSK3 inhibitor, Tideglusib, promoted statistically-significant increases (relative to siHes1 NPs alone) in siHes1 NP regenerative efficacy at a concentration of 10 µM in the middle turn and at concentrations of 2 and 10 µM in the basal turn of the OC. In the mid-apical region, where the siHes1 NP regenerative response was consistently highest, no statistically-significant differences between the treatment groups could be assigned. Due to the lack of a regenerative response induced by Tideglusib alone, the enhanced therapeutic effect induced by this combinatorial treatment strategy can be described as synergistic with respect to therapeutic increases in HC numbers.

Example 5-Additional Nanoparticle Experiments siHes1(Molecule #1)—loaded poly(lactic-co-glycolic acid) (PLGA) or polyethylene glycol-PLGA nanoparticles (PEG-PLGA NPs) were prepared by the water-in-oil-in-water (w/o/w) double emulsion solvent evaporation method with a slight modification, as previously reported. McCall and Sirianni (2013) *J Vis Exp.* 82: 51015; doi: 10.3791/51015.

Briefly, a volume of siHes1 aqueous solution (100 μL) was dropped in 1,000 μL of dichloromethane (DCM) containing 100 mg of PLGA for PLGA NPs or 50 mg of PLGA and 50 mg of PEG-PLGA for PEG-PLGA NPs (Table 1).

The mixture was emulsified by sonication (10 sec, 25W) (Microson ultrasonic cell disruptor XL Misonix Inc., Farmingdale, N.Y.) into a primary $w_1$/o emulsion. For PLGA NPs, the primary emulsion was diluted in 4 ml aqueous 5% PVA. The resulting secondary emulsion was diluted in 50 mL of 0.3% (w/v) (PLGA NPs) or 0.125% PVA (w/v) (PEG-PLGA NPs) in MilliQ water (Millipore Co., Billerica, Mass.) and magnetically stirred for two hours at room temperature (RO 10, IKA-Werke Gmbh & Co, Staufen, Germany) to evaporate the DCM. PEG-PLGA NPs were collected by ultracentrifugation at 13,000 g for 20 min at 10° C. (TOMY MX-201 Highspeed Refrigerated Microcentrifuge), washed thrice with MilliQ water to remove the excess of solvent (DCM) and residual PVA, then resuspended in 5 mL of MilliQ water in a sterile glass container, and freeze-dried at −100° C. under 40 mTorr (Virtis Benchtop freeze-dryer, Gardiner, N.Y.) for three consecutive days.

The obtained powdered NPs were sterilized under UV for 20-30 min and stored at −80° C. until further use.

TABLE 1

Formulation parameters of siHes1-loaded nanoparticles.

| | PLGA (mg) | PEG-PLGA (mg) | PVA (%) |
|---|---|---|---|
| siHes1-PLGA NPs | 100 | 0 | 5 |
| siHes1-PEG-PLGA NPs | 50 | 50 | 0.125 | siHes1-loaded PEGylated PLGA NPs (Table 2) were smaller (i.e. reduced particle mean diameters [PMD]) and less negatively charged (i.e. increased zeta potentials [ZP]) than the standard PLGA formulation. The amount of siHes1 (pmol/mg) loaded into the PEG-PLGA nanoparticle formulation was proportionally reduced with the decreased size of the nanocarrier relative to the PLGA formulation.

TABLE 2

Comparative physicochemical properties of representative formulations of Hes1 siRNA-loaded PLGA and PEG-PLGA NPs synthesized in parallel.

| Formulation | PMD (nm) | ZP (mV) | siHes1 Loading (pmol/mg) |
|---|---|---|---|
| siHes1-PLGA NPs | 325.4 ± 8.3 | −31.9 ± 3.5 | 143.9 ± 1.1 |
| siHes1-PEG-PLGA NPs | 182.5 ± 19.2 | −13.6 ± 3.3 | 82.02 ± 0.7 |

Based on their size and physicochemical properties, we hypothesized that siRNA-loaded PEG-PLGA NPs would be readily endocytosed by inner ear cells. In order to evaluate this hypothesis and compare uptake of siRNA-loaded PEG-PLGA NPs relative to PLGA NPs in inner ear cells, fluorescein (FAM)—conjugated non-targeting siRNA mimetics (scrambled RNA, scRNA) duplexes were encapsulated within AlexFluor 555-conjugated PEG-PLGA and PLGA NP formulations, using the same synthesis methodology as that employed for synthesizing siHes1 NPs. Prior to synthesis, the conjugation of Alexa Fluor 555 (AF555, MW: 1.25 kDa, Thermofisher, Rockford, Ill.) with PLGA (MW: 15 kDa) (Polymers Material Inc., Montréal, Canada) was performed using carbodiimide coupling reaction Chan et al. (2010) *Methods Mol Biol.* 624:163-75. Equimolar amounts of PLGA and AF555 were mixed and stirred overnight at room temperature. The unreacted components were removed by dialysis (Spectra/por Float-A-Lyzer G2, MWCO 3.5-5 kDa Spectrum Laboratories Inc. Rancho Dominguez, Calif.) against deionized water (Direct-Q 3 UV system, Millipore SAS, Molsheim, France), at room temperature for 3h. The purified suspension containing PLGA conjugated AF555 was recovered in purified water and centrifugated at 15,000 rpm for 30 min at 8° C. Post-synthesis, the resultant FAM-scRNA-loaded AlexaFluor555 PLGA or PEG-PLGA NPs (henceforth referred to as Dual Fluor NPS) were comparable in size, charge, and residual PVA content, as siHes1-loaded NPs, indicating that they were competent for serving as viable surrogates for the siHes1 nanocarrier formulations (Table 3).

TABLE 3

Comparative physicochemical properties of representative formulations of dual fluorophore-labeled non-targeting siRNA-loaded PLGA and PEG-PLGA NPs synthesized in parallel.

| Formulation | PMD (nm) | Zeta potential (mV) |
|---|---|---|
| Dual Fluor-PLGA NPs | 267.37 ± 14.8 | −36.6 |
| Dual Fluor-PEG-PLGA NPs | 184.88 ± 7.4 | −11.7 |

The cellular uptake of Dual Fluor PLGA and PEG-PLGA NPs were examined in the IMO-2b1 murine inner ear cell following a 24 h incubation at 33° C., 5% $CO_2$, using a combination of ultraviolet spectrometry-spectrometry (UV-spec) and confocal microscopy.

Figure 29:
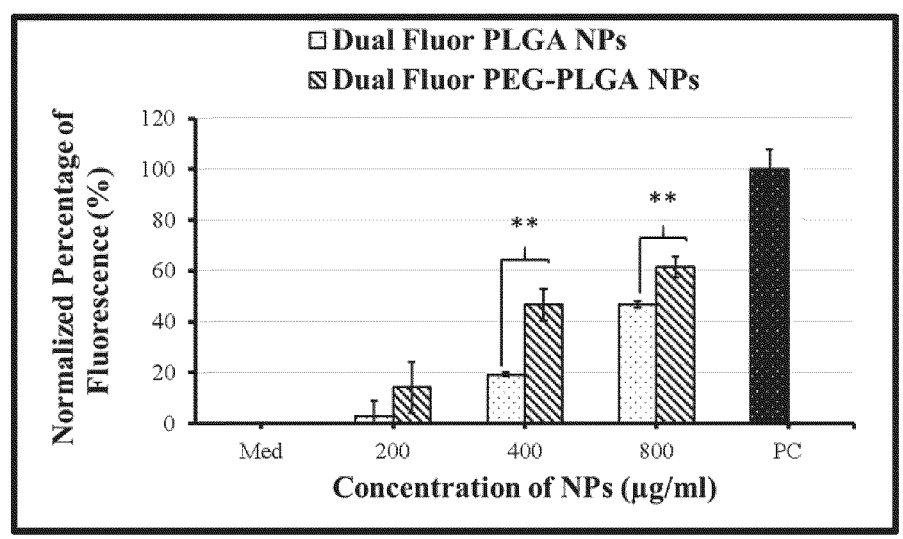
FIG. 29 depicts a graph that demonstrates dose-dependent uptake of fluorophore-conjugated siRNA-loaded PEG-PLGA NPs in IMO-2b1 inner ear cells.

For UV-spec, cells were seeded in 96-well plates and cultured in a complete growth medium to reach 70% confluence. After 24 h, cells were incubated with 200, 400, 800 μg/mL at 33° C., 5% $CO_2$ for 24 h. After three-step washing with PBS solution, the extracellular fluorescence was quenched with 50 μl of 0.2% Trypan Blue for 1-5 min (Gibco, BRL, Grand Island, N.Y.) (Hed J. Methods for distinguishing ingested from adhering particles. *Methods Enzymol.* 1986;132:198-204). Internalized fluorescent intensity was determined using a microplate reader (Beckman Coulter DTX 880 Multimode Detector, Brea, Calif.) at emission wavelength of 485±20 nm and excitation of 525±25 nm for FAM scRNA and at emission wavelength of 555±20 nm and excitation of 572±25 nm for AF555 PLGA. Positive control (PC) wells in which the unwashed fluorescence of the incubated NP suspensions prior to media evacuation were used to establish the 100% fluorescence for each reference standard. Normal control (NC) wells of cells that were not incubated with Dual Fluor NP formulations were used as the background control. Microplate reader evaluations of NP uptake demonstrated that, at doses of 400 and 800 μg/mL, the PEG-PLGA NPs exhibited superior internalization relative to PLGA NPs (FIG. 29, **, p<0.01). At a concentration of 200 μg/mL, the total fluorescence intensity of internalized NPs was similar between the two formulations.

Figure 30:
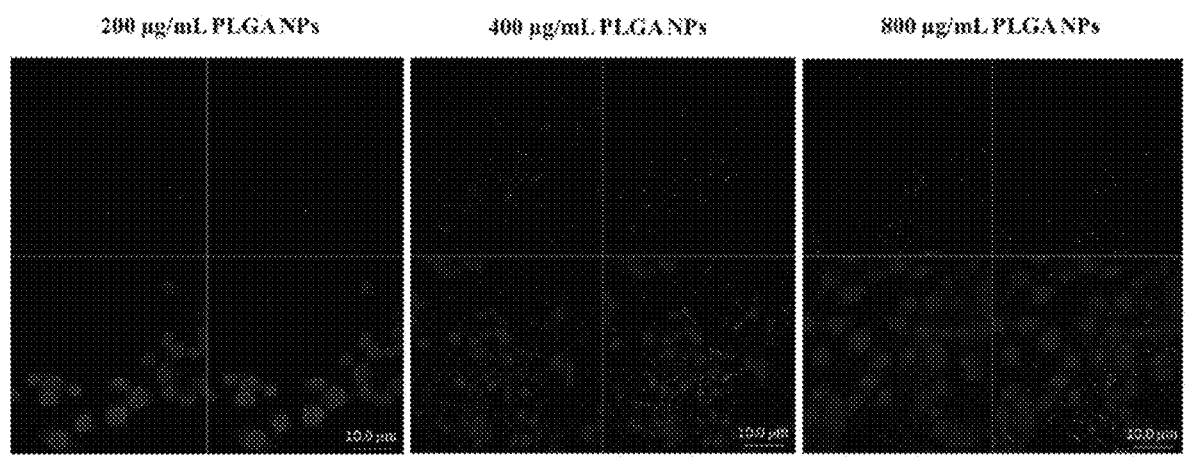
FIG. 30 depicts Dual Fluor PLGA NP internalization and localization in IMO-2b1 following a 24 h incubation with escalating doses (200, 400, or 800 µg/mL) of NPs prior to washing, fixation, and confocal microscopy imaging of FAM scRNA (green, upper left panel) and AF555-PLGA (red, upper right panel). Blue labeling (lower left panel) represents DAPI staining of cell nuclei. Merged images (lower right panel) depict overlap in signal (yellow) between scRNA and PLGA from internalized NPs. Scale bar is 10 µm and applies to all images.
Figure 31:
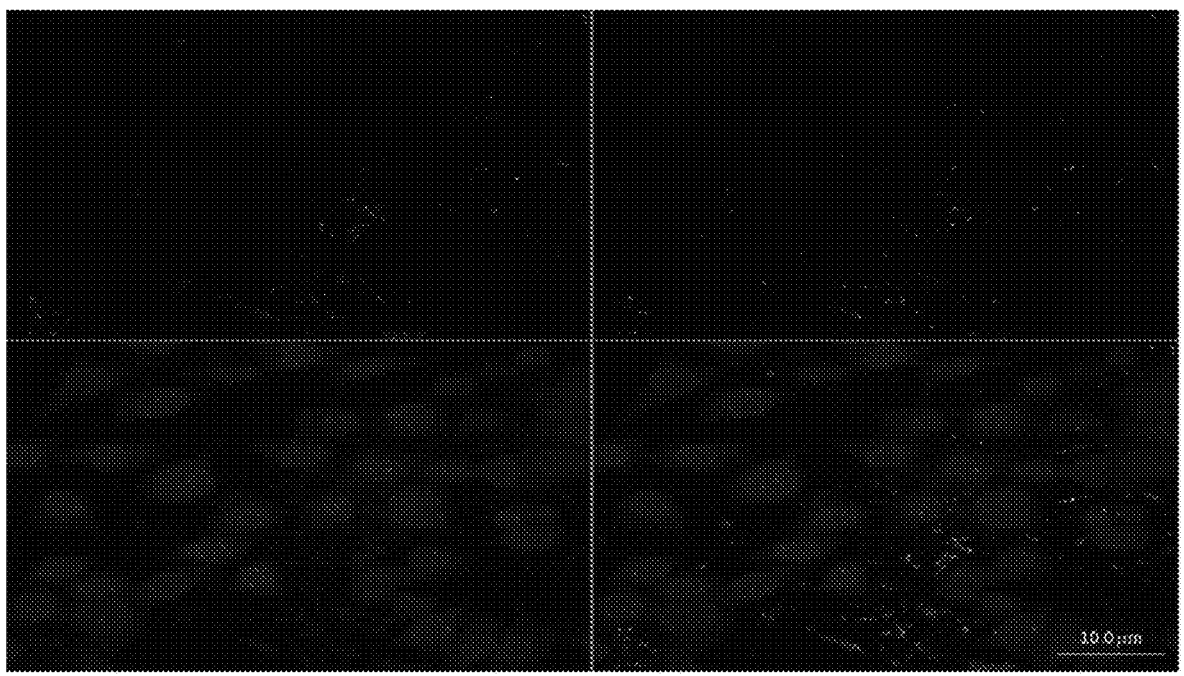
FIG. 31 depicts an enlargement of the 800 µg/mL confocal image set from FIG. 30.
Figure 32:
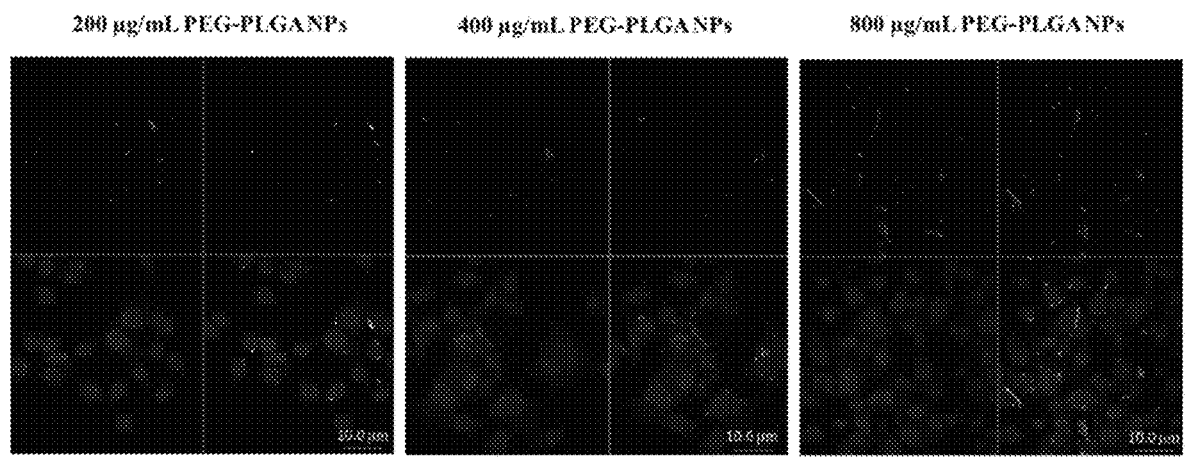
FIG. 32 depicts Dual Fluor PEG-PLGA NP internalization and localization in IMO-2b1 cells following a 24 h incubation with escalating doses (200, 400, or 800 µg/mL) of NPs prior to washing, fixation and confocal microscopy imaging of FAM scRNA (green, upper left panel) and AF555-PLGA (red, upper right panel). Blue labeling (lower left panel) represents DAPI staining of cell nuclei. Merged images (lower right panel) depict overlap in signal (yellow) between scRNA and PEG-PLGA from internalized NPs. Scale bar is 10 µm and applies to all images.
Figure 33:
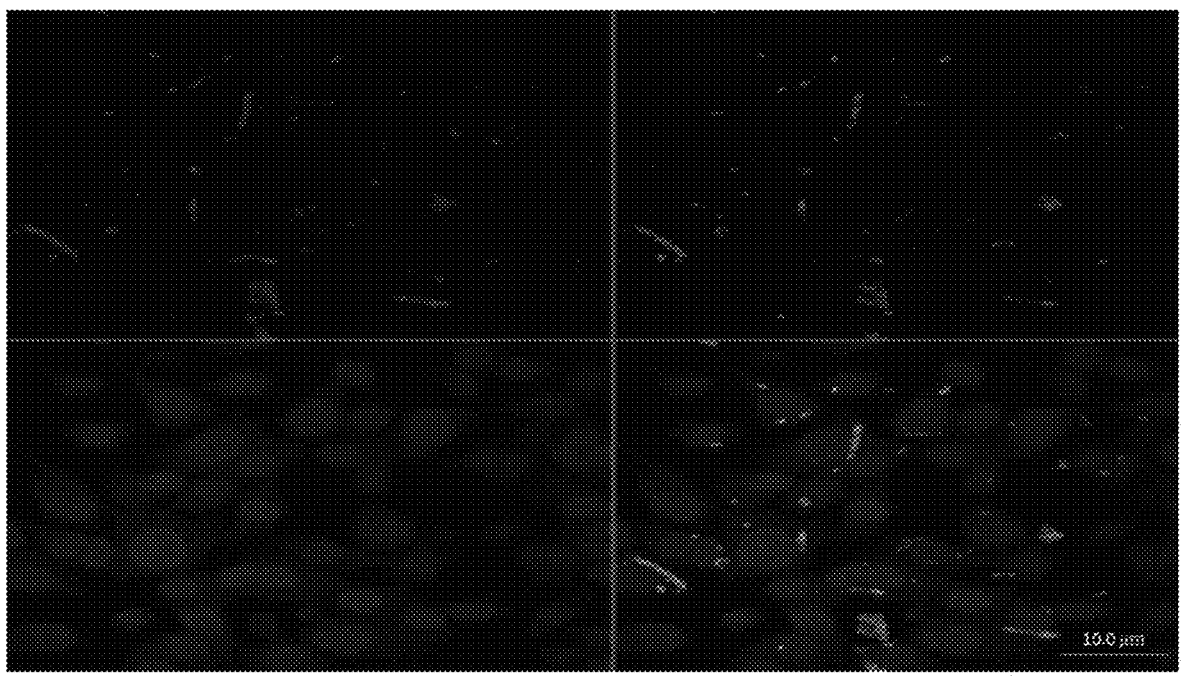
FIG. 33 depicts an enlargement of the 800 µg/mL confocal image set from FIG. 32.

Confocal microscopy of IMO-2b1 fixed cells following a 24 h incubation with fluorophore-labeled NPs confirmed both formulations were internalized within cells in a dose-dependent manner (FIG. 30). While siRNA-loaded PLGA NPs exhibited a heterodisperse localization pattern within IMO-2b1 cells, the equivalent PEG-PLGA NP formulation exhibited a more consistent perinuclear localization than the PLGA NPs (FIGS. 30-33). This observation suggests a more efficient delivery and accumulation of siRNA biomolecules delivered by PEG-PLGA NPs in a subcellular region that is optimal for siRNA-mediated gene silencing (Chiu et al. (2004) *Chem. Biol.* 11(8):1165-75).

Figure 34:
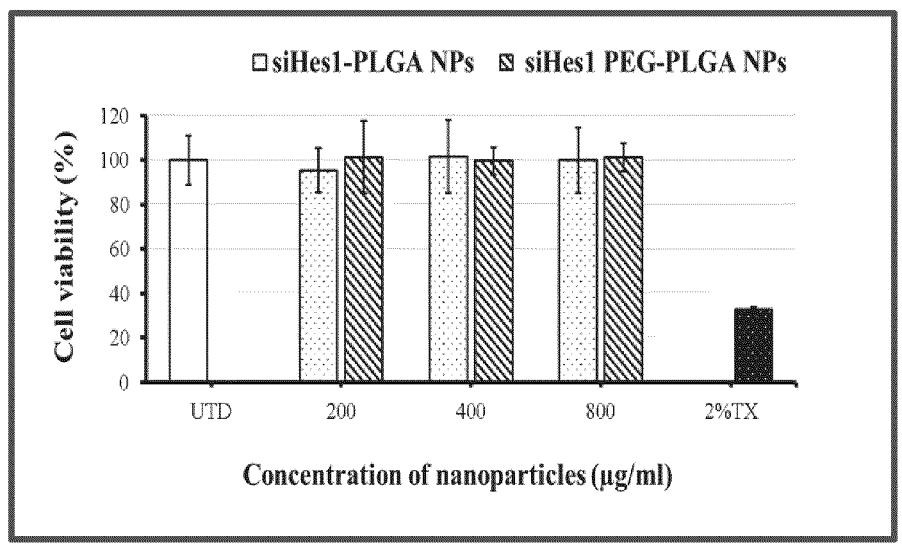
FIG. 34 depicts the results from an evaluation of the potential cytotoxic effects from dose-escalations of the new siHes1-loaded PEG-PLGA NP formulation on inner ear cell viability.

To evaluate potential cytotoxic effects of the siHes/-loaded PEG-PLGA NP formulation, IMO-2b1 cells were incubated with either PLGA or PEG-PLGA formulations for 48 h prior to conducting a 3-(4,5-dimethylthiazol-2-yl)-2,5-diphenyltetrazolium bromide (MTT) assay to assess cell viability. The MTT assay is a colorimetric method for objectively quantitating cell metabolic capacity by measuring NAD(P)H-dependent cellular oxidoreductase activity via reduction of a yellow tetrazolium dye, MTT, into its insoluble purple product, formazan. As such, the relative cytotoxic effects of a drug under evaluation can be discerned by comparing the amount of total formazan product formed in the test wells with the corresponding amount formed in control wells of untreated cells. Using this method, dose escalations up to 800 μg/mL (~66 nM siRNA equivalents) of siHes1-loaded PEG-PLGA NPs were well-tolerated by IMO-2b1 cells following a 48 h exposure (FIG. 34). At the highest concentration tested, no statistically-significant loss of cell viability was observed, using the MTT assay for either NP formulation compared to untreated controls (UTD). In contrast, wells treated with cytotoxic levels (2%) of the nonionic detergent, TritonX-100 (TX) showed marked loss of cell viability in this assay.

To test the relative silencing efficiency of the siHes1 biomolecule (Molecule #1) encapsulated within PEG-PLGA NPs, dose escalations of either siRNA-loaded PLGA and PEG-PLGA NPs were cultured with sub-confluent wells of IMO-2B1 cells, such that pair-wise dosing controlled for total siRNA in each well (28.8, 57.6, 115.2 nM siRNA equivalents). Seventy-two hours after initiation of NP treatment, total RNA was isolated and subjected to RT-qPCR analyses, using primers against Hes1 and the house keeping gene GAPDH. Relative Hes1 levels were determined by the $2^{-\Delta\Delta CT}$ method. See Livak and Schmittgen (2001)*Methods* 25(4):402-8.

Figure 35:
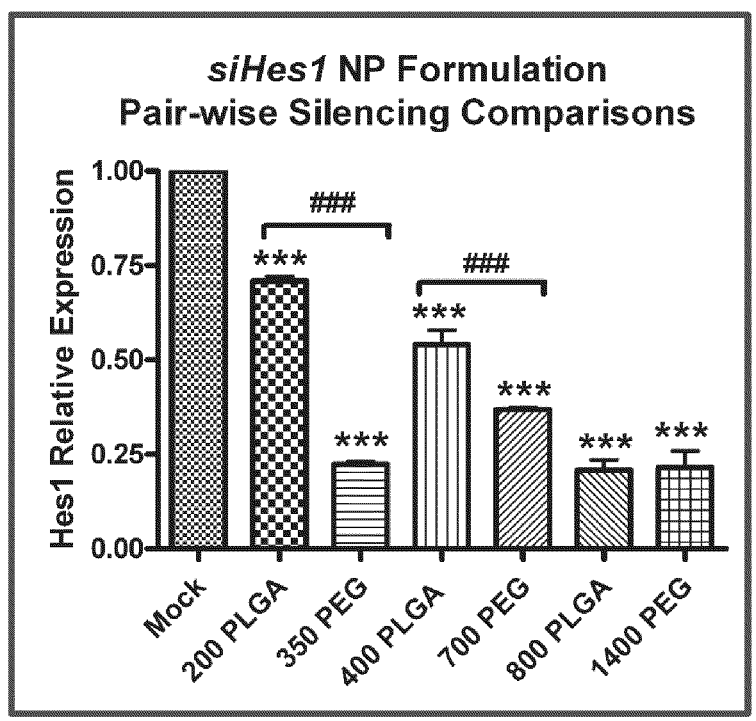
FIG. 35 depicts the results from a pair-wise comparative evaluation of the relative Hes1 silencing efficiency in inner ear cells achieved via dose-escalations of the new siHes1-loaded PEG-PLGA NP formulation relative to siHes1-loaded PLGA NPs.

Consistent with its apparent enhanced uptake efficiency and functionally-optimal perinuclear accumulation pattern, PEG-PLGA NPs loaded with siHes1 (Molecule #1) elicited a more pronounced silencing effect on Hes1 expression at low-dose equivalents than did PLGA NPs (FIG. 35, ###, $p<0.001$ with respect to degree of silencing induced by PEG-PLGA NPs relative to PLGA NPs at the indicated doses).

Figure 36:
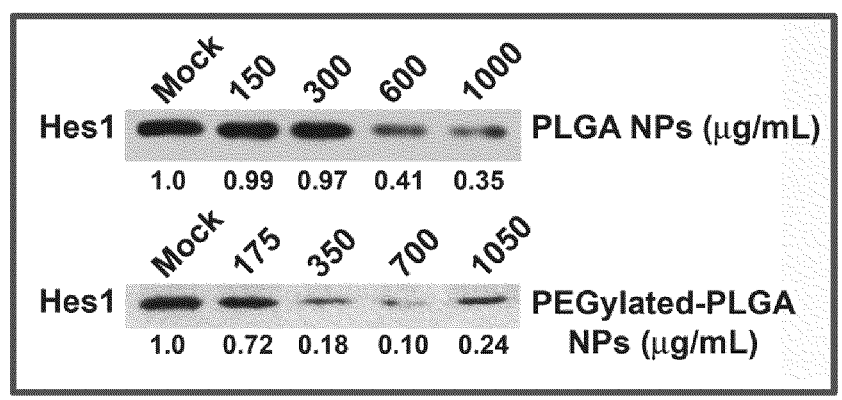
FIG. 36 depicts the results from comparative evaluations of relative Hes1 silencing efficiency at the protein level in inner ear cells achieved via dose-escalations of the new siHes1-loaded PEG-PLGA NP formulation relative to siHes1-loaded PLGA NPs synthesized in parallel.

Targeted comparisons of siHes1 KD efficiency in IMO-2b1 at the protein level (96 h post-exposure) mirrored the results obtained from measurements of Hes1 at the transcript level (72 h post-exposure) (FIG. 36). Post-NP incubation, cell extracts were subjected to immunoblotting with an antibody against Hes1, and relative levels of Hes1 in the immunoblots were determined by densitometric analyses using NIH Image J software. The numbers below each lane represent the amount of Hes1 protein measured in each extract relative to the untreated (Mock) control samples in each blot. At concentrations, of 350 μg/mL and above, marked reductions in Hes1 protein were observed for the PEGylated-PLGA NPs, whereas clear reductions in Hes1 levels for PLGA NPs were first observed at 600 μg/mL and above.

Example 6-Duration of Administration Experiments

Figure 39:
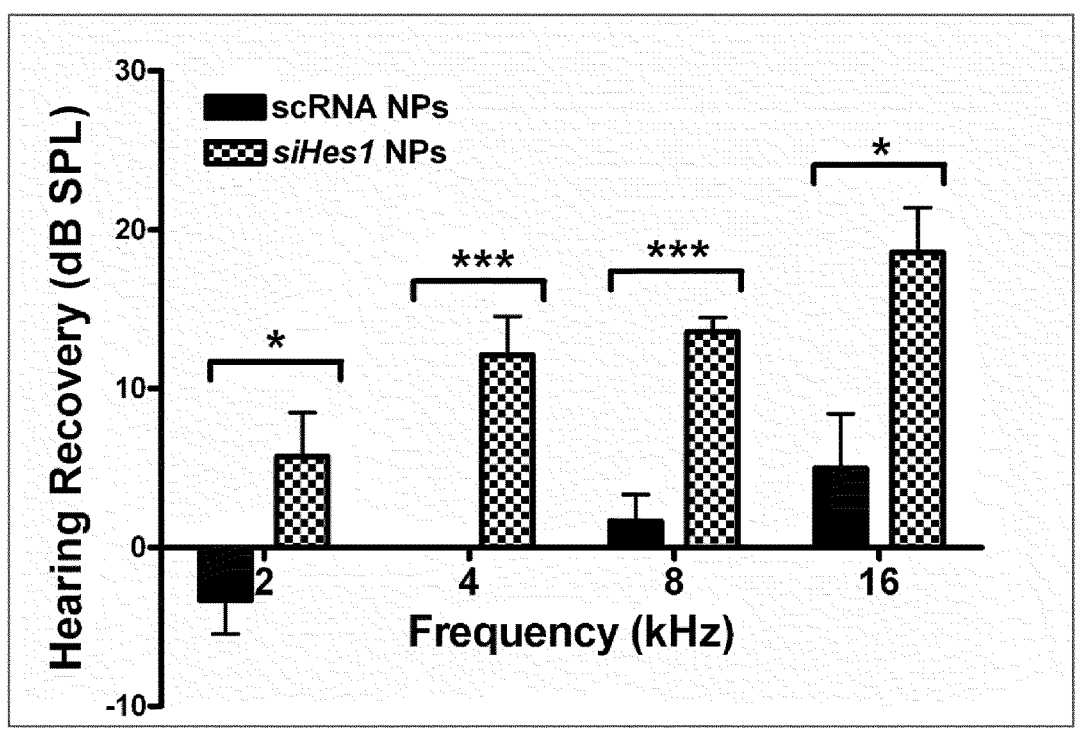
FIG. 39 shows the results of a one-day infusion of siHES1 nanoparticles on the restoration of hearing function in noise-deafened guinea pigs. Guinea pigs were exposed to deafening noise levels (125 dB SPL octave band noise centered at 4 kHz) for three hours. Seventy-two hours after the acoustic trauma, PLGA NPs (800 µg/mL) loaded with either sham (i.e. non-targeting scrambled RNA, scRNA) or therapeutic Hes1 siRNA (siHes1) were delivered into the cochleae (cochleostomy) by mini-osmotic pumps at a speed of 1.0 µL per hour over the course of 24 h (one-day infusion). Auditory brain stem response (ABR) measurements were recorded at three weeks post-treatment, and mean ABR threshold recoveries (i.e hearing recovery compared to one day after the acoustic overexposure) were plotted across test frequencies of 2-16 kHz for each group. While the damaging noise exposure induced pronounced hearing loss (i.e. high ABR threshold shifts) across all test frequencies, siHes1 NP-treated ears exhibited a significant improvement in threshold recovery across the entire 2-16 kHz range relative to scRNA NP-treated ears (* and ***, p<0.05 and 0.001; n=6 for each group).
Figure 40:
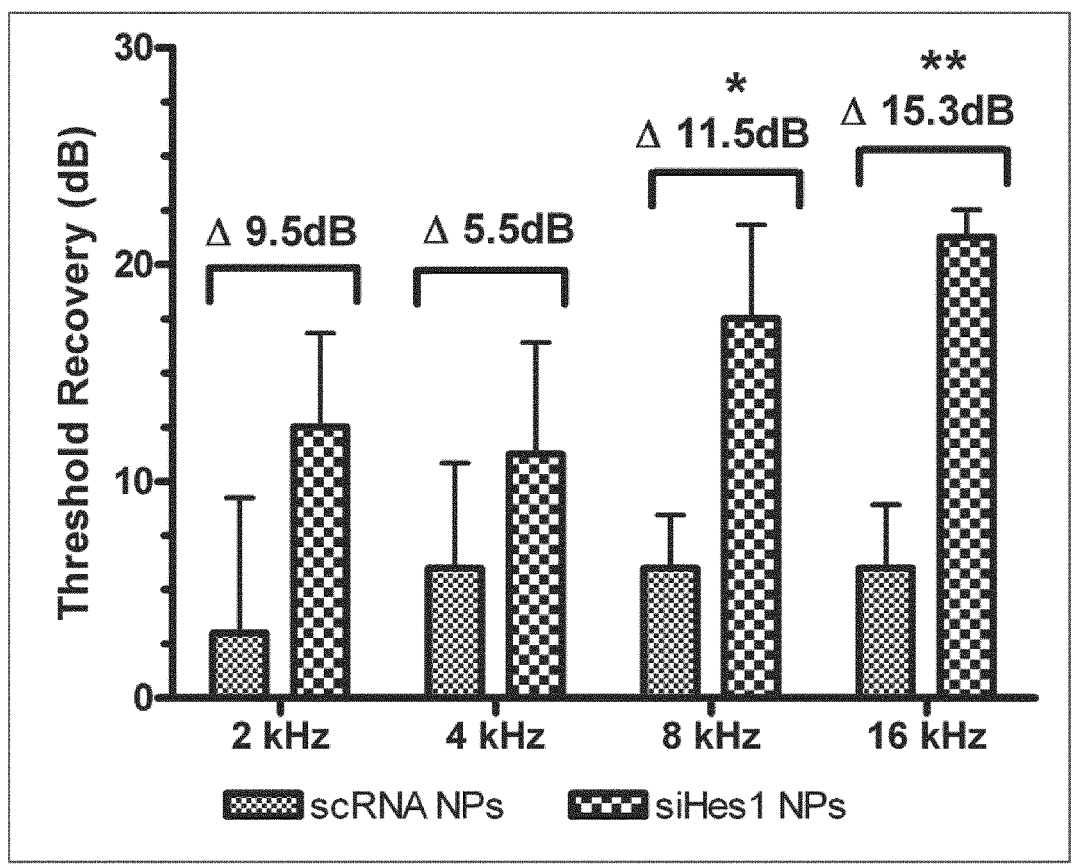
FIG. 40 shows differences in ABR threshold recovery in live guinea pigs post-deafening following delayed (72 h post-injury) therapeutic intervention with either scRNA NPs or siHES1 NPs in vivo in surgically-infused (one-day administration) ears at nine weeks after treatment compared to one day after the acoustic overexposure at test frequencies of 2, 4, 8, and 16 kHz. The degree of siHES1 NP treatment-specific improvement on threshold recovery observed here would be predicted to be of clinical significance (*p<0.05, **p<0.01).
Figure 41:
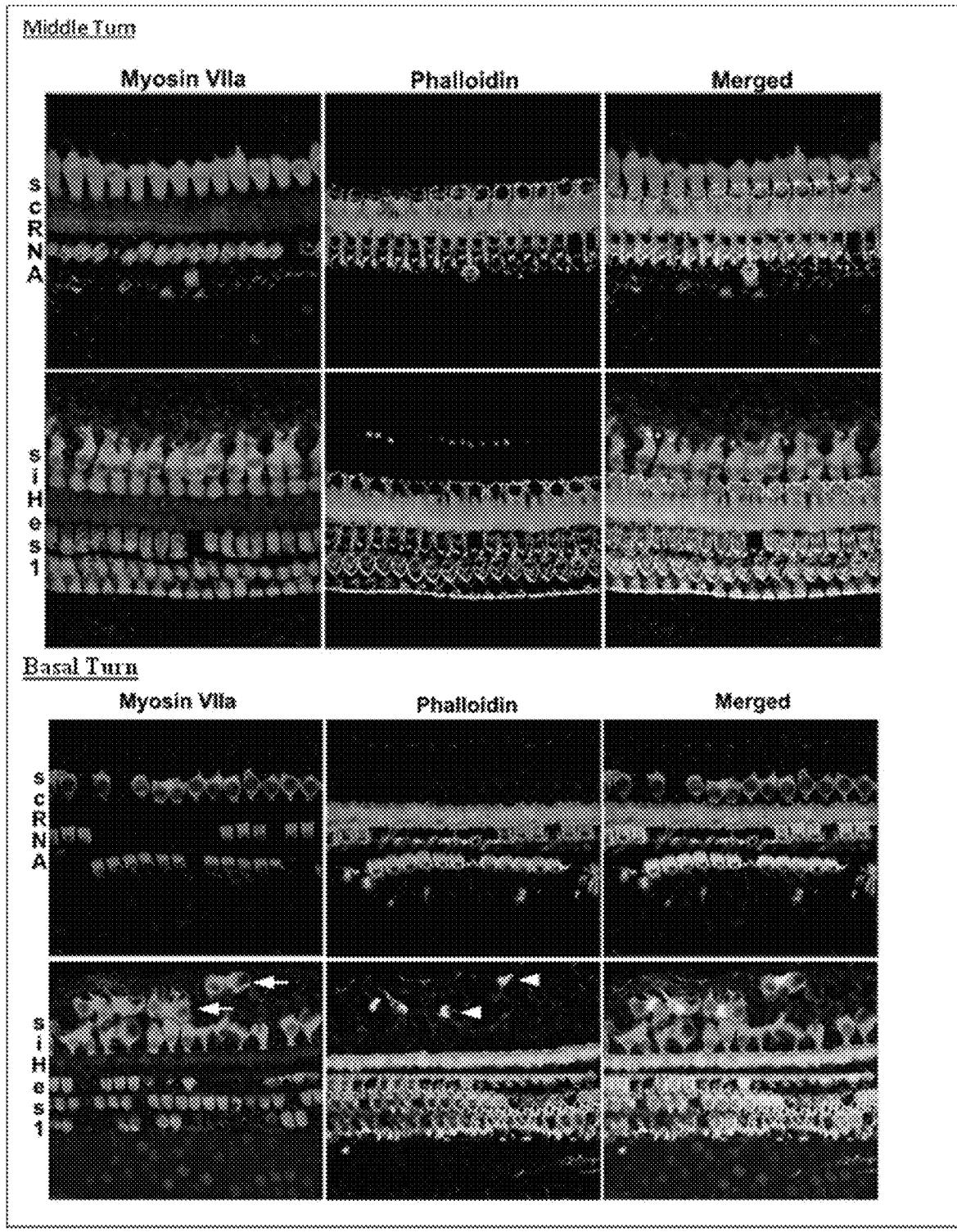
FIG. 41 demonstrates that siHES1 NP treatment restores HC numbers in the basal turn of the cochlea from treated ears in noise-exposed mature pigmented guinea pigs. Myo7a- and Phalloidin-labeling in sham (scRNA) and (si-Hes1) NP-treated ears revealed pronounced loss of OHCs in scRNA NP-infused ears and marked recovery of OHC numbers in siHes1 NP-treated ears in both the middle and basal turns of noise-ablated guinea pig cochleae. Arrows denote the occurrence of ectopic Myo7a-positive HCs bearing stereociliary bundles (arrowheads) uniquely observed in the IHC region in siHes1 NP-treated ears, consistent with de novo production of morphologically-mature HCs.

Duration of therapeutic dosing of siHes1 NPs was tested in follow-up experimentation by limiting administration to only one day (24 h), initiated 72 h post-deafening. As seen in FIG. 39, substantial, statistically-significant hearing improvement was observed across multiple test frequencies as early as three-weeks post-infusion using this alternative administration paradigm. As depicted in FIG. 40, substantial hearing improvement was also observed over an extended nine-week period, with the greatest progressive improvement in the high frequency, basal region. These results revealed that a one-day siHes1 NP infusion was seemingly as efficacious as a ten-day infusion for restoring auditory function in noise-deafened animals. While this result was somewhat surprising, it suggests that the NP-mediated delivery of siHes1 results in efficient loading of the siRNA into the endogenous multiprotein RNA-induced silencing complex (RISC) in this context, which, once loaded, can sustain gene silencing for weeks at a time following a single dose administration in non-dividing cells. See Wei et al. (2011) *Mol Pharmacol.* 79(6):953. PubMed PMID: 21427169; Bartlett et al. (2006) *Nucleic Acids Res.* 34(1):322. Epub 2006/01/18. PubMed PMID: 16410612; PMCID: 1331994; Bartlett et al. (2007) *Biotechnol Bioeng.* 97(4):909. PubMed PMID: 17154307.

Similar experiments are repeated with the combination therapies described herein.

What is claimed is:

1. A method of treating hearing loss or balance dysfunction in a subject comprising:
   applying to the inner ear of a subject in need thereof an effective amount of a GSK-3 inhibitor, and,
   applying to the inner ear of said subject an amount of a composition comprising an siRNA molecule sufficient to decrease the expression of a Hes1 gene in a tissue of the inner ear,
   wherein the composition comprising an siRNA molecule is applied either i) separately after an application of the GSK-3 inhibitor or ii) with an application of the GSK-3 inhibitor but in which the composition mimics a staged application.

2. The method of claim 1, wherein the GSK-3 inhibitor is selected from 6-bromoindirubin-3'-oxime (BIO) and tideglusib (TIDE).

3. The method of claim 1, wherein the siRNA molecule comprises one or more of pairs of sequences selected from the group consisting of SEQ ID NO: 1, and SEQ ID NO: 2; (b) SEQ ID NO: 3 and SEQ ID NO: 4; (c) SEQ ID NO: 5 and SEQ ID NO: 6; (d) SEQ ID NO: 7 and SEQ ID NO: 8; (e) SEQ ID NO: 9 and SEQ ID NO: 10; (f) SEQ ID NO: 11 and SEQ ID NO: 12; (g) SEQ ID NO: 13 and SEQ ID NO: 14.

4. The method of claim 1, wherein the composition that mimics a staged application comprises a sustained release formulation.

5. The method of claim 1, further comprising applying to the inner ear of a subject in need thereof an effective amount of FGF2.

6. The method of claim 1, wherein one or more of the applying steps comprise transtympanic administration, intracochlear injection, intracochlear infusion, or using ear drops.

7. The method of claim 4, wherein the sustained release formulation comprises a nanoparticle comprising an siRNA molecule that decreases expression of a Hes1 gene in a tissue of the inner ear.

8. The method of claim 4, wherein the sustained release formulation comprises a lipofection complex comprising an siRNA molecule that decreases expression of a Hes1 gene in a tissue of the inner ear.

9. The method of claim 7, wherein the nanoparticle further comprises a biodegradable polymer.

10. The method of claim 9, wherein the biodegradable polymer comprises poly(lactic-co-glycolic acid) (PLGA) or pegylated PLGA (PEG-PLGA).

11. The method of claim 7, wherein the nanoparticle further comprises a magnetically responsive particle.

12. The method of claim 11, wherein the magnetically responsive particle comprises superparamagnetic iron oxide (SPION).

13. The method of claim 11, further comprising using magnetic force to transport the nanoparticles across the round or oval window membrane.

14. A method of replacing, regenerating, and/or protecting hair cells in the inner ear of a subject comprising:
   applying to the inner ear of a subject in need thereof an effective amount of an inhibitor of GSK3, a fibroblast growth factor, or combinations thereof, and
   applying to the inner ear of said subject an amount of a composition comprising an siRNA molecule sufficient to decrease the expression of a Hes1 gene in a tissue of the inner ear,
   wherein the composition comprising an siRNA molecule is applied either i) separately after an application of the GSK-3 inhibitor or ii) with an application of the GSK-3 inhibitor but in which the composition mimics a staged application.

15. The method of claim 14, wherein the GSK-3 inhibitor is selected from 6-bromoindirubin-3'-oxime (BIO) and tideglusib (TIDE).

16. The method of claim 14, wherein the fibroblast growth factor comprises FGF2.

17. The method of claim 14, wherein the siRNA molecule comprises one or more of pairs of sequences selected from the group consisting of SEQ ID NO:
   1, and SEQ ID NO: 2; (b) SEQ ID NO: 3 and SEQ ID NO: 4; (c) SEQ ID NO: 5 and SEQ ID NO: 6; (d) SEQ ID NO: 7 and SEQ ID NO: 8; (e) SEQ ID NO: 9 and SEQ ID NO: 10; (f) SEQ ID NO: 11 and SEQ ID NO: 12; (g) SEQ ID NO: 13 and SEQ ID NO: 14.

18. The method of claim 14, wherein the composition that mimics a staged application comprises a sustained release formulation.

19. The method of claim 14, wherein either or both applying steps comprise transtympanic administration, intracochlear injection, intracochlear infusion, or using ear drops.

20. The method of claim 18, wherein the sustained release formulation comprises a nanoparticle comprising an siRNA molecule that decreases expression of a Hes1 gene in a tissue of the inner ear.

21. The method of claim 18, wherein the sustained release formulation comprises a lipofection complex comprising an siRNA molecule that decreases expression of a Hes1 gene in a tissue of the inner ear.

22. The method of claim 20, wherein the nanoparticle further comprises a biodegradable polymer.

23. The method of claim 22, wherein the biodegradable polymer comprises poly(lactic-co-glycolic acid) (PLGA) or pegylated PLGA (PEG-PLGA).

24. The method of claim 20, wherein the nanoparticle further comprises a magnetically responsive particle.

25. The method of claim 24, wherein the magnetically responsive particle is superparamagnetic iron oxide (SPION).

26. The method of claim 24, further comprising using magnetic force to transport the nanoparticles across the round or oval window membrane.

* * * * *

SEQUENCE LISTING

```
<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 1
cagcugauau aauggagaat t                                             21
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 2
uucuccauua uaucagcugt t                                                   21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 3
gaagggcaag aauaaaugat t                                                   21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 4
ucauuuauuc uugcccuuct t                                                   21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 5
gaugccaaag auguuugaat t                                                   21

-continued

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 6
uucaaacauc uuuggcauct t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 7
caacacgaca ccggauaaat t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 8
uuuauccggu gucguguugt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 9

```
ggauugcgcc uuuguauuat t                                              21
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 10

```
uaauacaaag gcgcaauccu t                                              21
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 11

```
gcucagauga cauuucguut t                                              21
```

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 12

```
aacgaaaugu caucugagct t                                              21
```

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13

```
acugcaugac ccagaucaa                                                 19
```

<210> SEQ ID NO 14
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 14
uugaucuggg ucaugcagu                                                      19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 15
gcaucaacag cagcauagat t                                                   21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 16
ucuaugcugc uguugaugct t                                                   21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 17
ggucauucuu agagaaugut t                                                   21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

-continued

```
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 18
acauucucua agaaugacct t                                             21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 19
cgaugauccu uaaaggauut t                                             21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 20
aauccuuuaa ggaucaucgt t                                             21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 21
ugcugacucc aaagcucugt t                                             21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

-continued

```
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 22
cagagcuuug gagucagcat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (20)..(21)
<223> OTHER INFORMATION: May or may not be present

<400> SEQUENCE: 23
ggguauucuu ggaucuccat t                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uggagaucca agaauaccca g                                              21

<210> SEQ ID NO 25
<211> LENGTH: 280
<212> TYPE: PRT
<213> ORGANISM: Homo sapiens

<400> SEQUENCE: 25

Met Pro Ala Asp Ile Met Glu Lys Asn Ser Ser Pro Val Ala Ala
 1               5                  10                  15

Thr Pro Ala Ser Val Asn Thr Thr Pro Asp Lys Pro Lys Thr Ala Ser
                20                  25                  30

Glu His Arg Lys Ser Ser Lys Pro Ile Met Glu Lys Arg Arg Arg Ala
            35                  40                  45

Arg Ile Asn Glu Ser Leu Ser Gln Leu Lys Thr Leu Ile Leu Asp Ala
        50                  55                  60

Leu Lys Lys Asp Ser Ser Arg His Ser Lys Leu Glu Lys Ala Asp Ile
    65                  70                  75                  80

Leu Glu Met Thr Val Lys His Leu Arg Asn Leu Gln Arg Ala Gln Met
                85                  90                  95

Thr Ala Ala Leu Ser Thr Asp Pro Ser Val Leu Gly Lys Tyr Arg Ala
            100                 105                 110

Gly Phe Ser Glu Cys Met Asn Glu Val Thr Arg Phe Leu Ser Thr Cys
        115                 120                 125

Glu Gly Val Asn Thr Glu Val Arg Thr Arg Leu Leu Gly His Leu Ala
    130                 135                 140
```

-continued

Asn Cys Met Thr Gln Ile Asn Ala Met Thr Tyr Pro Gly Gln Pro His
145                 150                 155                 160

Pro Ala Leu Gln Ala Pro Pro Pro Pro Gly Pro Gly Gly Pro
            165                 170                 175

Gln His Ala Pro Phe Ala Pro Pro Pro Leu Val Pro Ile Pro Gly
            180                 185                 190

Gly Ala Ala Pro Pro Gly Gly Ala Pro Cys Lys Leu Gly Ser Gln
            195                 200                 205

Ala Gly Glu Ala Ala Lys Val Phe Gly Gly Phe Gln Val Val Pro Ala
210                 215                 220

Pro Asp Gly Gln Phe Ala Phe Leu Ile Pro Asn Gly Ala Phe Ala His
225                 230                 235                 240

Ser Gly Pro Val Ile Pro Val Tyr Thr Ser Asn Ser Gly Thr Ser Val
                245                 250                 255

Gly Pro Asn Ala Val Ser Pro Ser Gly Pro Ser Leu Thr Ala Asp
            260                 265                 270

Ser Met Trp Arg Pro Trp Arg Asn
275                 280

<210> SEQ ID NO 26
<211> LENGTH: 166
<212> TYPE: PRT
<213> ORGANISM: Homo sapiens

<400> SEQUENCE: 26

Met Ala Pro Ser Thr Val Ala Val Glu Leu Leu Ser Pro Lys Glu Lys
1               5                   10                  15

Asn Arg Leu Arg Lys Pro Val Val Glu Lys Met Arg Arg Asp Arg Ile
                20                  25                  30

Asn Ser Ser Ile Glu Gln Leu Lys Leu Leu Leu Glu Gln Glu Phe Ala
            35                  40                  45

Arg His Gln Pro Asn Ser Lys Leu Glu Lys Ala Asp Ile Leu Glu Met
        50                  55                  60

Ala Val Ser Tyr Leu Lys His Ser Lys Ala Phe Val Ala Ala Gly
65                  70                  75                  80

Pro Lys Ser Leu His Gln Asp Tyr Ser Glu Gly Tyr Ser Trp Cys Leu
                85                  90                  95

Gln Glu Ala Val Gln Phe Leu Thr Leu His Ala Ala Ser Asp Thr Gln
            100                 105                 110

Met Lys Leu Leu Tyr His Phe Gln Arg Pro Ala Ala Pro Ala Ala
        115                 120                 125

Pro Ala Lys Glu Pro Lys Ala Pro Gly Ala Ala Pro Pro Ala Leu
130                 135                 140

Ser Ala Lys Ala Thr Ala Ala Ala Ala His Gln Pro Ala Cys
145                 150                 155                 160

Gly Leu Trp Arg Pro Trp
                165

<210> SEQ ID NO 27
<211> LENGTH: 360
<212> TYPE: PRT
<213> ORGANISM: Homo sapiens

<400> SEQUENCE: 27

Met Ala Ala Ala Ala Ala Gly Ala Gly Pro Glu Met Val Arg Gly
1               5                   10                  15

-continued

```
Gln Val Phe Asp Val Gly Pro Arg Tyr Thr Asn Leu Ser Tyr Ile Gly
             20                  25                  30
Glu Gly Ala Tyr Gly Met Val Cys Ser Ala Tyr Asp Asn Val Asn Lys
         35                  40                  45
Val Arg Val Ala Ile Lys Lys Ile Ser Pro Phe Glu His Gln Thr Tyr
 50                  55                  60
Cys Gln Arg Thr Leu Arg Glu Ile Lys Ile Leu Leu Arg Phe Arg His
 65                  70                  75                  80
Glu Asn Ile Ile Gly Ile Asn Asp Ile Ile Arg Ala Pro Thr Ile Glu
                 85                  90                  95
Gln Met Lys Asp Val Tyr Ile Val Gln Asp Leu Met Glu Thr Asp Leu
                100                 105                 110
Tyr Lys Leu Leu Lys Thr Gln His Leu Ser Asn Asp His Ile Cys Tyr
            115                 120                 125
Phe Leu Tyr Gln Ile Leu Arg Gly Leu Lys Tyr Ile His Ser Ala Asn
130                 135                 140
Val Leu His Arg Asp Leu Lys Pro Ser Asn Leu Leu Leu Asn Thr Thr
145                 150                 155                 160
Cys Asp Leu Lys Ile Cys Asp Phe Gly Leu Ala Arg Val Ala Asp Pro
                165                 170                 175
Asp His Asp His Thr Gly Phe Leu Thr Glu Tyr Val Ala Thr Arg Trp
                180                 185                 190
Tyr Arg Ala Pro Glu Ile Met Leu Asn Ser Lys Gly Tyr Thr Lys Ser
            195                 200                 205
Ile Asp Ile Trp Ser Val Gly Cys Ile Leu Ala Glu Met Leu Ser Asn
210                 215                 220
Arg Pro Ile Phe Pro Gly Lys His Tyr Leu Asp Gln Leu Asn His Ile
225                 230                 235                 240
Leu Gly Ile Leu Gly Ser Pro Ser Gln Glu Asp Leu Asn Cys Ile Ile
                245                 250                 255
Asn Leu Lys Ala Arg Asn Tyr Leu Leu Ser Leu Pro His Lys Asn Lys
                260                 265                 270
Val Pro Trp Asn Arg Leu Phe Pro Asn Ala Asp Ser Lys Ala Leu Asp
            275                 280                 285
Leu Leu Asp Lys Met Leu Thr Phe Asn Pro His Lys Arg Ile Glu Val
290                 295                 300
Glu Gln Ala Leu Ala His Pro Tyr Leu Glu Gln Tyr Tyr Asp Pro Ser
305                 310                 315                 320
Asp Glu Pro Ile Ala Glu Ala Pro Phe Lys Phe Asp Met Glu Leu Asp
                325                 330                 335
Asp Leu Pro Lys Glu Lys Leu Lys Glu Leu Ile Phe Glu Glu Thr Ala
                340                 345                 350
Arg Phe Gln Pro Gly Tyr Arg Ser
            355                 360
```